United States Patent
Rothpearl et al.

(10) Patent No.: US 8,489,410 B2
(45) Date of Patent: *Jul. 16, 2013

(54) SYSTEM AND METHOD FOR MODIFYING AND ROUTING DICOM EXAMINATION FILES

(75) Inventors: Allen Rothpearl, Roslyn Heights, NY (US); John Killcommons, Garden City, NY (US); Rafael Sanguinetti, Westbury, NY (US)

(73) Assignee: Medimaging Tools, LLC, Westbury, NY (US)

( * ) Notice: Subject to any disclaimer, the term of this patent is extended or adjusted under 35 U.S.C. 154(b) by 560 days.

This patent is subject to a terminal disclaimer.

(21) Appl. No.: 11/627,779

(22) Filed: Jan. 26, 2007

(65) Prior Publication Data

US 2007/0203748 A1     Aug. 30, 2007

Related U.S. Application Data

(63) Continuation-in-part of application No. 11/358,254, filed on Feb. 21, 2006, now Pat. No. 8,140,350.

(60) Provisional application No. 60/655,331, filed on Feb. 22, 2005, provisional application No. 60/661,773, filed on Mar. 15, 2005, provisional application No. 60/670,326, filed on Apr. 12, 2005.

(51) Int. Cl.
G06Q 10/00     (2012.01)

(52) U.S. Cl.
USPC .................................................. 705/2; 705/3

(58) Field of Classification Search
USPC .......................................................... 705/2
See application file for complete search history.

(56) References Cited

U.S. PATENT DOCUMENTS

| | | | |
|---|---|---|---|
| 5,005,126 A | 4/1991 | Haskin | |
| 5,296,688 A | 3/1994 | Hamilton et al. | |
| 5,590,271 A | 12/1996 | Klinker | |
| 5,734,915 A | 3/1998 | Roewer | |
| 5,740,267 A | 4/1998 | Echerer et al. | |
| 5,851,186 A * | 12/1998 | Wood et al. | 600/437 |
| 5,986,662 A | 11/1999 | Argiro et al. | |
| 5,987,345 A | 11/1999 | Engelmann et al. | |
| 6,006,191 A | 12/1999 | DiRienzo | |
| 6,241,668 B1 | 6/2001 | Herzog | |
| 6,260,021 B1 * | 7/2001 | Wong et al. | 705/2 |
| 6,424,996 B1 | 7/2002 | Killcommons et al. | |
| 6,574,629 B1 | 6/2003 | Cooke, Jr. et al. | |
| 6,609,135 B1 * | 8/2003 | Omori et al. | 707/104.1 |
| 6,611,846 B1 | 8/2003 | Stoodley | |
| 6,621,918 B1 | 9/2003 | Hu et al. | |
| 6,678,703 B2 | 1/2004 | Rothschild et al. | |
| 6,708,189 B1 | 3/2004 | Fitzsimons et al. | |

(Continued)

Primary Examiner — Michael Fuelling
(74) Attorney, Agent, or Firm — Ostrolenk Faber LLP

(57) ABSTRACT

The invention comprises a system and method for receiving a DICOM image file from a first DICOM storage service class user, employing rules on the DICOM image file and forwarding the DICOM image file to a second DICOM storage service class user in accordance with the rules. After router configuration information, remote server configuration information, routing rules information and replacement rules information is received from a user, a DICOM image file received over a communication network from the first DICOM storage service class user in accordance with the router configuration information is modified in accordance with the replacement rules information, and the modified DICOM image file is routed to the at least one computing device in accordance with the routing rules.

22 Claims, 27 Drawing Sheets

U.S. PATENT DOCUMENTS

| | | |
|---|---|---|
| 6,785,410 B2 | 8/2004 | Vining et al. |
| 6,819,785 B1 | 11/2004 | Vining et al. |
| 6,879,411 B1 | 4/2005 | Otsuka et al. |
| 2001/0041991 A1 | 11/2001 | Segal et al. |
| 2002/0001401 A1 | 1/2002 | Bocionek |
| 2002/0016718 A1 | 2/2002 | Rothschild et al. |
| 2002/0019751 A1 | 2/2002 | Rothschild et al. |
| 2002/0055917 A1 | 5/2002 | Muraca |
| 2002/0102028 A1 | 8/2002 | Keller et al. |
| 2002/0131625 A1 | 9/2002 | Vining et al. |
| 2003/0208564 A1 | 11/2003 | Miyake et al. |
| 2004/0017475 A1 | 1/2004 | Akers et al. |
| 2004/0078337 A1 | 4/2004 | King et al. |
| 2004/0111297 A1 | 6/2004 | Schoenberg |
| 2005/0002483 A1 | 1/2005 | Wilcox, Jr. |
| 2006/0149600 A1 | 7/2006 | Cavanaugh et al. |

* cited by examiner

| Email | Fax cover | Id | Institution | Modality | Patient Name | Study date |
|---|---|---|---|---|---|---|
| | Create FaxCover | 972 | U.S. DIAGNOSTIC | MR | ABAYEV^SLAVIK | 20051102 |
| | Create FaxCover | 1652 | Spine and Joint Bronx | MR | ABBATE,STEVEN-43 | 20051110 |
| | Create FaxCover | 1670 | Spine and Joint Bronx | MR | ABBATE,STEVEN-43 | 20051110 |
| | Create FaxCover | 1637 | Central Radiology Services | MR | ABDUL-RAHMAN, QAISEERAH | 20051116 |
| | Create FaxCover | 587 | Western Nassau Diagnostic Imaging Machine 8 | US | ABITINO,MARIO^ARTERIAL | 20051109 |
| | Create FaxCover | 500 | Central Radiology Services | MR | ABOUHAJI, KAMAL | 20051115 |
| | Create FaxCover | 1779 | Spine and Joint Bronx | MR | ABREGO,KAIN-24 | 20051116 |
| | Create FaxCover | 1744 | Spine and Joint Bronx | MR | ABREGO,KAIN-24-LT | 20051116 |
| | Create FaxCover | 1221 | Central Radiology Services | MR | ABREU, JOSE | 20051118 |
| | Create FaxCover | 887 | Western Nassau Diagnostic Imaging Machine 2 | US | ACETO,ANTHONY^ABD | 20051117 |
| | Create FaxCover | 842 | WESTERN NASSAU DIAGNOSTIC IMAGING | US | acker,elizabeth^abd | 20051108 |

SYSTEM AND METHOD FOR MODIFYING AND ROUTING DICOM EXAMINATION FILES

CROSS-REFERENCE TO RELATED APPLICATIONS

The present application is a continuation-in-part of U.S. patent application Ser. No. 11/358,254, filed on 21, February, 2006 and entitled "SYSTEM AND METHOD FOR INTEGRATING ANCILLARY DATA IN DICOM IMAGE FILES," which is based on and claims priority to U.S. Provisional Patent Application Ser. No. 60/655,331, filed on Feb. 22, 2005 and entitled "SYSTEM AND METHOD FOR INTEGRATING ANCILLARY DATA IN DICOM IMAGE FILES," and which further claims priority to U.S. Provisional Patent Application Ser. No. 60/661,773, filed on Mar. 15, 2005 and entitled "SYSTEM AND METHOD FOR INTEGRATING ANCILLARY DATA IN DICOM IMAGE FILES (II)," and which further claims priority to U.S. Provisional Patent Application Ser. No. 60/670,326, filed on Apr. 12, 2005 and entitled "SYSTEM AND METHOD FOR INTEGRATING ANCILLARY DATA IN DICOM IMAGE FILES (III)," the entire contents of all of which are hereby incorporated by reference.

BACKGROUND OF THE INVENTION

1. Field of the Invention

The present invention relates, generally, to medical image records, and, more particularly, to modifying and routing DICOM image files with medical information to at least one or more sources.

2. Description of the Related Art

The Digital Imaging and Communications in Medicine (DICOM) standard was created by the National Electrical Manufacturers Association (NEMA) for improving distribution and access of medical images, such as CT scans, MRI and x-rays.

Accordingly, contemporary medical imaging uses the DICOM image format for the transport and storage of medical images. The DICOM image format arose in an attempt to standardize the image format of different machine vendors (i.e., GE, Hitachi, Philips) to promote compatibility such that machines provided by competing vendors could transmit and receive information between them. This original goal for the DICOM format has achieved varying degrees of success.

Over time, the DICOM standard has become the de-facto standard for the format used for medical images that are electronically transferred from one place to another. DICOM files have found particular use in the field of teleradiology. As used herein, the term "teleradiology" refers to, generally, the practice of reading a medical image at a location that is remote from the location where a medical examination was performed, or where the medical image related to the examination was acquired. Typically, the image is electronically transferred to the location where it is eventually read.

Teleradiologists (i.e., physicians who read and/or interpret medical images at a remote location) have encountered a major obstacle regarding images formatted according to the DICOM standard. Accurate interpretations of medical images require that the radiologist be aware of related patient information submitted by the referring physician. For example, a radiologist requires information regarding the patient's medical history, and perhaps information regarding the technologist and/or physician who performed the medical examination. The radiologist (and patient) will also benefit from having the referring physician's address, telephone and fax information readily available in order to communicate urgent findings or for use in secondary data feeds, such as the known Health Level 7 ("HL-7") protocol. As known to those skilled in the art, HL-7 is a standardized data protocol for data transmitted within the healthcare industry. Unfortunately, such information is not typically available and teleradiologists often encounter an obstacle because they cannot interpret patient examinations accurately in a vacuum.

In the prior art, the DICOM image format provides for the entry of brief patient histories, usually by the technologist, and may also provide a patient work-list by the technologist that includes patient history and/or physician information. However, in practice, such information is often not provided or used as intended. This occurs, typically, because technologists who are time-constrained, tend to omit data entry tasks that they perceive as overly time-consuming, and they rationalize that the radiologist who eventually reads and interprets the medical image(s) already has or can gain access easily to the patient's chart should the radiologist require more information than provided in the DICOM file. Unfortunately this assumption is often false, especially in a teleradiology practice, when the patient's chart may be located hundreds or thousands of miles from the location where the teleradiologist actually interprets the medical image and/or examination.

Solutions to problems associated with a teleradiologist requiring more information than is provided in a DICOM file have, for the most part, taken the form of faxing or scanning handwritten clinical data (i.e., paperwork) to the teleradiologist. In the case of scanning, paperwork is typically entered in a flatbed or sheet-fed scanner and the scanned, electronic image(s) of the paperwork is uploaded to a computer, such as to a server configured to receive files via the file transfer protocol ("FTP"). The scanned paperwork can then be transmitted to a remote computer and made available to the teleradiologist.

Unfortunately, such prior art solutions are cumbersome and often untenable, especially in cases involving more than just a few patients. Accordingly, some prior art software vendors providing DICOM files have incorporated some type of image capture software in their software packages that provides for scanning, and electronically integrating the scanned material into the DICOM image file. This prior art software, however, is typically designed for capturing secondary medical images, and not paperwork. Also, such software can be quite cumbersome to use and require many complex steps. Further, technologists who operate medical image software programs vary widely in their abilities to use difficult software. Many are unable to use the software successfully for various reasons, including respective skill levels.

Most teleradiologists agree that an ideal scenario involves the simultaneous viewing of hand-written paper data when medical images are being viewed and interpreted. This is preferred over reviewing paper data, not as a separate task. To date, little has been done to facilitate this goal.

Moreover, it is recognized by the inventors that the transmission of DICOM image files that are transmitted in a DICOM communication session often include various errors, including data errors and data format errors, which complicate one's ability to receive and process a DICOM image file. Further, certain tag information is often incorrectly specified, such as a window and/or level value. Moreover, certain older CT and MRI devices incorrectly populate DICOM data fields. Too often, discovery of such errors occurs during processing of a DICOM image file, which contributes increased frustration and associated costs. Often, similar or the same errors are repeated by the same sending DICOM service class user.

SUMMARY OF THE INVENTION

The foregoing illustrates the need for a system and method that automatically corrects and routes DICOM files to one or more DICOM storage service class users.

Accordingly, a system and method is provided for receiving a DICOM image file from a first DICOM storage service class user, employing rules on the DICOM image file and forwarding the DICOM image file to a second DICOM storage service class user in accordance with the rules.

More particularly and in a preferred embodiment, the system and method include receiving from a user via an electronic user interface router configuration information that represents at least a DICOM storage service class provider for receiving the DICOM image file from the first DICOM storage service class user. Further, the system and method include receiving from the user via the electronic user interface remote server configuration information that represents at least one computing device operable to send or receive DICOM image files.

Moreover, the system and method include receiving from the user via the electronic user interface routing rules information the routing rules information representing first data conditions that are to be examined to determine which of the at least one computing device the DICOM image file is to be transmitted. Also, the system and method include receiving from the user via the electronic user interface replacement rules information, the replacement rules information representing second data conditions that are to be examined to determine whether and how to modify at least one data value in the DICOM image file.

Also in a preferred embodiment, the method and system include receiving over a communication network the DICOM image file from the first DICOM storage service class user in accordance with the router configuration information, modifying the at least one data value in the DICOM image file in accordance with the replacement rules information, and routing the modified DICOM image file to the at least one computing device in accordance with the routing rules.

Furthermore, the router configuration information preferably includes at least one of a port number, a local application entity title, and a default server name. Also, the DICOM image filed is preferably received by a computing device represented by the default service name in the event no matching rules are met. Also in accordance with the teachings herein, the replacement rules information, the rules information, the remote server configuration information and the router configuration information are preferably stored in a database.

Other features in various embodiments include that the first and second data conditions are based upon values or formatting of data in DICOM data fields. Further, the router configuration information includes an internet protocol address, an application entity title, and a port number. Also, the DICOM image file is received and forwarded in one DICOM format.

Moreover, a rules-driven data application is provided that functions as a DICOM storage service class provider by receiving a DICOM image through a DICOM communication session. The application includes routing rules that define how to send a DICOM image to one or more servers and replacement rules that modify or replace one or more DICOM Tags in the DICOM image with new values. The routing rules and replacement rules operate to modify or route, or modify and route the DICOM image as a DICOM Storage Service Class User ("SCU") after the routing rules or replacement rules.

BRIEF DESCRIPTION OF THE DRAWINGS

For the purpose of illustrating the invention, there is shown in the drawings a form which is presently preferred, it being understood, however, that the invention is not limited to the precise arrangements and instrumentalities shown. The features and advantages of the present invention will become apparent from the following description of the invention that refers to the accompanying drawings, in which:

FIGS. 11A-11F illustrate example display screens and reports that are provided in accordance with an internet, web-based embodiment of the present invention.

DESCRIPTION OF THE EMBODIMENTS

The present invention comprises a system and method for incorporating paperwork/handwritten (analog) clinical patient information into digital DICOM image files for interpretation by the radiologist or other physician. In an example embodiment, the present invention comprises a suite of software modules which reads and incorporates paperwork/handwritten (analog) clinical patient information directly integrating them into the DICOM image examination files.

In an example embodiment of the present invention, patient demographic information is output as a separate file after a patient examination file is acquired by a DICOM server. This output file comprised of key available DICOM tags, contains demographic information of the patient along with detailed information regarding the examination itself. A key indexing number, for example, labeled the "Study UID" number, is preferably included among these DICOM tags in the output file. The present invention imports the output file from either a remote FTP site or a local folder, either in an automated fashion, or by user intervention with a GUI. Of course, one skilled in the art will recognize that other methods and locations for transferring and/or receiving electronic files are known, and are envisioned in the present invention. The present invention differs from prior art methods in its ability to utilize the DICOM tags, and in particular, the STUDY UID tag, and to have the analog data become a part of the original DICOM image examination, rather than merely an attachment to it.

Figure 1:
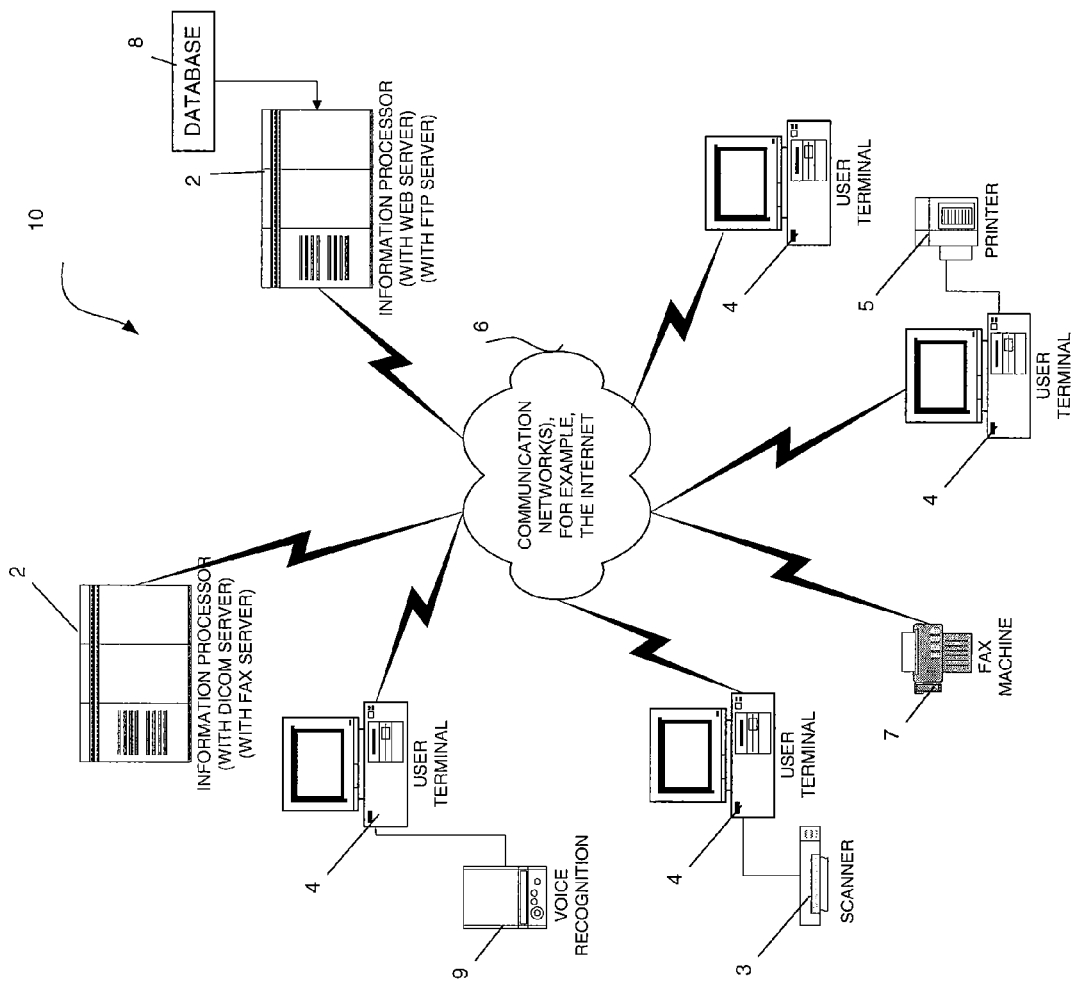
FIG. 1 shows an example hardware arrangement in a preferred embodiment of the present invention.

Referring to the drawings, in which like reference numerals refer to like elements, FIG. 1 shows an example hardware arrangement in a preferred embodiment of the present invention and referred to generally as system 10. In the embodiment shown in FIG. 1, system 10 comprises at least one information processor 2 configured to operate as an internet web server and/or file transfer protocol server ("FTP") that is operable to access and update a database 8. Information processor 2 preferably accesses communication network 6 and communicates with user terminals 4. Preferably, user terminals 4 and information processor(s) 2 communicate via the known communications protocol, Transmission Control Protocol/Internet Protocol "TCP/IP." In this way, content can be transmitted to and from the devices 2 and 4, and commands can be executed to enable the various functions described herein.

Information processors 2 and user terminals 4 are any devices that are capable of sending and receiving data across communication network 6, e.g., mainframe computers, mini computers, personal computers, laptop computers, a personal digital assistants (PDA) and internet access devices such as Web TV. In addition, information processors 2 and user terminals 4 are preferably equipped with a web browser, such as MICROSOFT INTERNET EXPLORER, NETSCAPE NAVIGATOR, MOZILLA FIRREFOX or the like. Thus, as envisioned herein, information processor 2 and/or user terminals 4 are devices that can communicate over a network and can be operated anywhere, including, for example, moving vehicles.

In a preferred embodiment of the present invention, various kinds input devices and output devices are utilized by system 10. Although many of the devices interface (e.g., connect) with a computer, it is envisioned herein that many of the device can operate without any direct connection to a computer. With reference to FIG. 1, scanner 3, fax machine 7 and voice recognition device 9 are operable to provide data to information processor 2. Further, printer 5 and fax machine 7 are operable to output data. Thus, a plurality of so-called "peripheral" devices are included in system 10 that provide data to and from information processor 2 and user terminal 4.

The nature of the present invention is such that one skilled in the art of writing computer executable code (i.e., software) can implement the described functions using one or more of a combination of popular computer programming languages and developing environments including, but not limited to C, C++, Visual Basic, JAVA, PHP, HTML, XML, ACTIVE SERVER PAGES, JAVA server pages, servlets, MICROSOFT .NET, and a plurality of various web site development applications.

For example, data may be configured in a MICROSOFT EXCEL spreadsheet file, as a comma delimited ASCII text file, as a MICROSOFT SQL SERVER compatible table file (e.g., MS-ACCESS table), or the like. In another embodiment, data may be formatted as an image file (e.g., TIFF, JPG, BMP, GIF, or the like). In yet another embodiment, data may be stored in an ADOBE ACROBAT PDF file. Preferably, one or more data formatting and/or normalization routines are provided that manage data received from one or a plurality of sources. In another example, data are received that are provided in a particular format (e.g., MICROSOFT EXCEL), and programming routines are executed that convert the data to another formatted (e.g., ASCII comma-delimited text).

It is contemplated herein that any suitable operating system can be used on user terminals 4 and information processor 2, for example, DOS, WINDOWS 3.x, WINDOWS 95, WINDOWS 98, WINDOWS NT, WINDOWS 2000, WINDOWS ME, WINDOWS CE, WINDOWS POCKET PC, WINDOWS XP, MAC OS, UNIX, LINUX, PALM OS, POCKET PC or any other suitable operating system. Of course, one skilled in the art will recognize that other software applications are available in accordance with the teachings herein, including, for example, via JAVA, JAVA Script, Action Script, Swish, or the like.

Moreover, a plurality of data file types is envisioned herein. For example, the present invention preferably supports various suitable multi-media file types, including (but not limited to) JPEG, BMP, GIF, TIFF, MPEG, AVI, SWF, RAW or the like (as known to those skilled in the art).

Preferably, the present invention comprises a rules-driven application that acts as a DICOM Storage Service Class Provider ("SCP"), receiving images through a DICOM communication session, substantially as described herein. Preferably, at least two types of rules are supported that are user-defined: 1) routing rules and 2) replacement rules. The routing rules enable a DICOM image to be transmitted to one or more servers. The replacement rules enable one or more DICOM Tags to be modified or replaced with new values, automatically. When combined with the routing rules, the replacement rules make an extremely powerful and versatile DICOM router that is operable to modify and/or route a DICOM examination after replacing one or more DICOM fields as a function of specific pre-defined set of criteria. Moreover, the present invention preferably performs rules interpretation, tag modification, and routing substantially automatically and immediately, thereby sending a modified DICOM image to a DICOM Storage Service Class User ("SCU") in response to rules interpretation and/or tag replacement. Discussions of the rules and respective implementations in a preferred embodiment are provided below.

Figure 2:
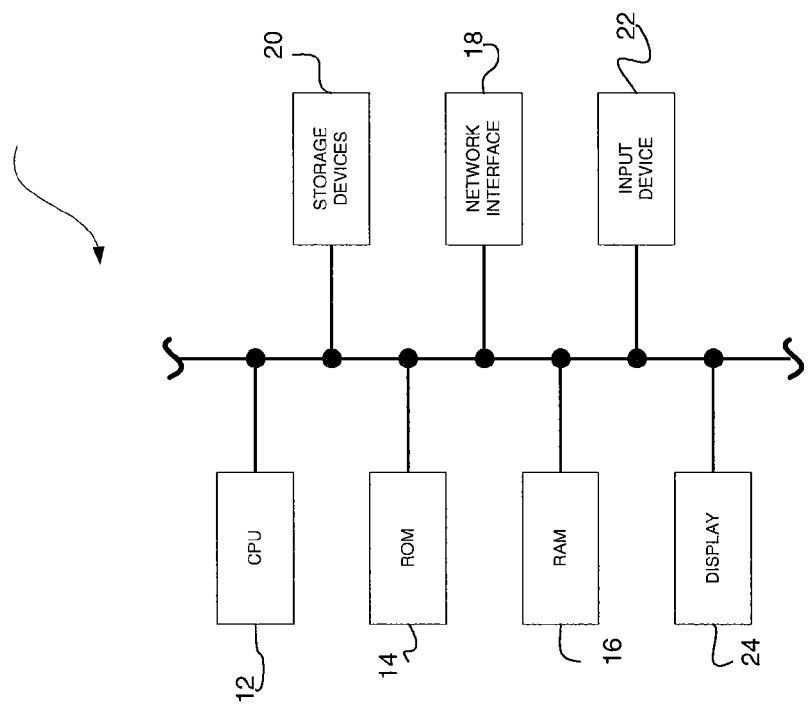
FIG. 2 illustrates the functional elements of a user terminal and/or information processor.

FIG. 2 illustrates the functional elements of user terminal 4 and/or information processor 2 and that include one or more central processing units (CPU) 12 used to execute software code and control the operation of user terminal 4, read-only memory (ROM) 14, random access memory (RAM) 16, one or more network interfaces 18 to transmit and receive data to and from other computing devices across a communication network, storage devices 20 such as a hard disk drive, floppy disk drive, tape drive, CD ROM or DVD for storing program code, databases and application data, one or more input devices 22 such as a keyboard, mouse, track ball, magnetic card reading device, bar code reading device, microphone or the like, and a display 24.

The various components of information processor 2 and/or user terminal 4 need not be physically contained within the same chassis or even located in a single location. For example, storage device 20 may be located at a site which is remote from the remaining elements of information processor 2 or user terminal 4, and may even be connected to CPU 12 across communication network 6 via network interface 18. Information processor 2 preferably includes a memory equipped with sufficient storage to provide the necessary databases, forums, and other community services as well as acting as a web server for communicating hypertext markup language (HTML), FLASH, Action Script, Java, Active Server Pages, Active-X control programs on user terminals 4. Information processors 2 are arranged with components, for example, those shown in FIG. 2, suitable for the expected operating environment of information processor 2. The CPU(s) 12, network interface(s) 18 and memory and storage devices are selected to ensure that capacities are arranged to accommodate expected demand.

As used herein, the terms, "module" and "submodule" refer, generally, to one or more discrete components that contribute to the effectiveness of the present invention. Modules can operate or, alternatively, depend upon one or more other modules in order to function.

In an example embodiment, the present invention provides a graphical user interface that includes a drop-down list (or other graphical screen control) of patient names (or other identifiers) for the user to select a patient. After the above-described output file is received, patient information in the output file is extracted and used to populate the drop-down list. The automated version allows a faxed or hand-scanned copy of this paperwork to automatically perform a database lookup for the patient, and automatically associate itself with the DICOM tags for the patient (including the Study UID) and upload itself to become part of the DICOM image examination without user intervention. More specifically, both the manually operated and the automated version of the invention allows an electronic version of the paperwork, for example paperwork that is scanned in a sheet fed or auto-feed scanner, or faxed from a fax machine, to be associated with a particular patient examination, and uploaded to a DICOM server where the imaging examination resides, as part of the imaging examination itself. In other words, the present invention electronically associates and integrates electronic versions of paperwork with one or more medical images. The electronic DICOM file representing the examination is opened by the radiologist (or teleradiologist) or other physician for interpretation, and the clinical patient paperwork displays simultaneously, thereby allowing the viewing of patient information at the same time that the digital medical image(s) are viewed and interpreted.

The present invention preferably includes one or more software modules and/or ancillary software applications. For example, the invention provides a module which auto-uploads data files to a remote DICOM server. Another module functions as a sort of file daemon that monitors one or more locations on a computer system for the existence of a data file. When a data file is discovered, the data are automatically processed and/or uploaded, and converted (if necessary) to the JPEG file format and then processed. For example, a technologist scans paperwork to a Tag Image File Format ("TIFF") file, or faxes paperwork to the file directory, and the modules of the present invention discover the TIFF file, convert it to a JPEG file, and upload it to a server where it is processed for further manipulation, substantially as described herein.

Figure 3:
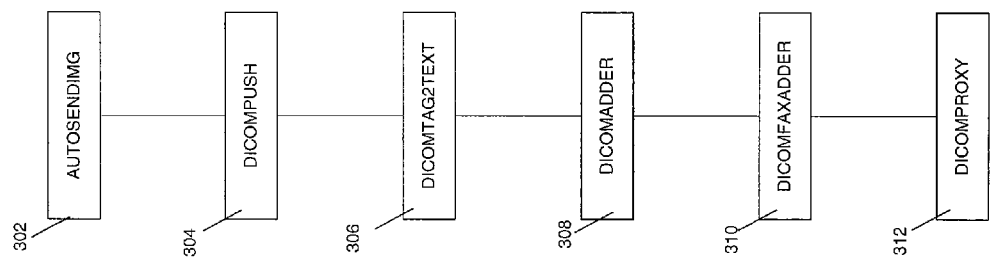
FIG. 3 is a block diagram showing example software modules in accordance with a preferred embodiment of the present invention.

The following discussion regards example software modules, which are represented in the block diagram shown in FIG. 3, and operable in an embodiment of the present invention. The following discussion of example software modules makes reference to example display screens shown in FIGS. 4A-4K. In accordance with a preferred embodiment, many of the screen displays provided by the present invention are formatted as graphical controls, such as textboxes, checkboxes, dropdown lists, pushbuttons, radio buttons or the like. Many of the display screens provided by the present invention are operable as data entry forms, and information provided in the form is preferably stored in database 8. Of course, one skilled in the art will recognize that the example modules and corresponding names are illustrative, and that various other designs, names and modules may be fashioned depending upon a particular embodiment of the present invention.

FIG. 3 is a block diagram illustrating various modules and respective parameters in accordance with an example embodiment of the present invention. It is preferred that the modules illustrated in FIG. 3 operate together as an integrated unit, and incorporate various utilities, described below, for operation. Although the modules are designed to operate together, the modules can be used individually in cases where an integrated interface is not useable for any reason.

Module AUTOSENDIMG 302 determines when an image file, such as a TIFF file or JPEG file, is stored in a specified file folder. When an image file is recognized, module 302 preferably converts it to DICOM format and transmits the formatted file to DICOM Server 2. In a preferred embodiment, module 302 recognizes when the name of the image file employs a particular format, such as PatientName-PatientID-StudyUID (e.g., names of data fields that represent a patient and study), and module 302 preferably uses these data when converting an image file to the DICOM format. Moreover, module 302 preferably references an American Standard Code for Information Interchange ("ASCII") text file (e.g., named "config.txt") in order to retrieve and add information, such as Institution Name, Study Description and Modality.

Figure 4A:
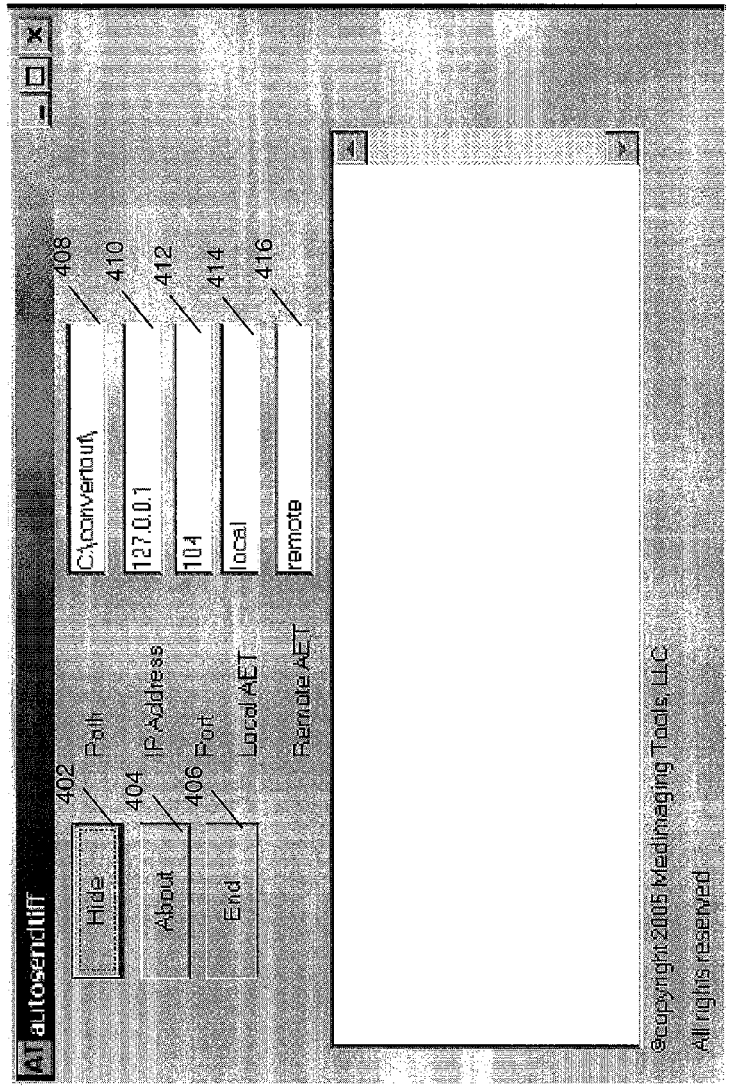
FIGS. 4A-4K illustrates example display screens provided by the software modules shown in FIG. 3 and provided in accordance with a preferred embodiment of the present invention.

In accordance with the MICROSOFT WINDOWS operating system, module 302 preferably operates as a background application and is represented by an icon in the MICROSOFT WINDOWS system tray. When the icon is selected, a user interface, substantially as shown in FIG. 4A, is displayed. As shown in FIG. 4A, selecting hide button 402 causes display screen 400 to be removed from view (e.g., referred to in the art as being minimized). Selecting About button 404 displays textual information regarding module 302, and selecting the End button 406 terminates module 302. In addition, parameters are preferably defined by a user and referenced by module 302: Path name 408, IP address 410, Port Number 412, Local Entity Title 414 and DICOM server Entity Title 416. For example, Path name 408 represents a folder that is used by module 302 to determine where an image file that requires conversion to DICOM format is stored. IP Address 410 represents the IP address of the DICOM Server 2 where the image file properly formatted in the DICOM format, is to be transmitted. Port Number 412 represents the port number of the DICOM Server 2. Local Entity Title 414 and Server Entity Title 414 represent the respectively designated names of the local computer system and the remote server 2.

Figure 4B:
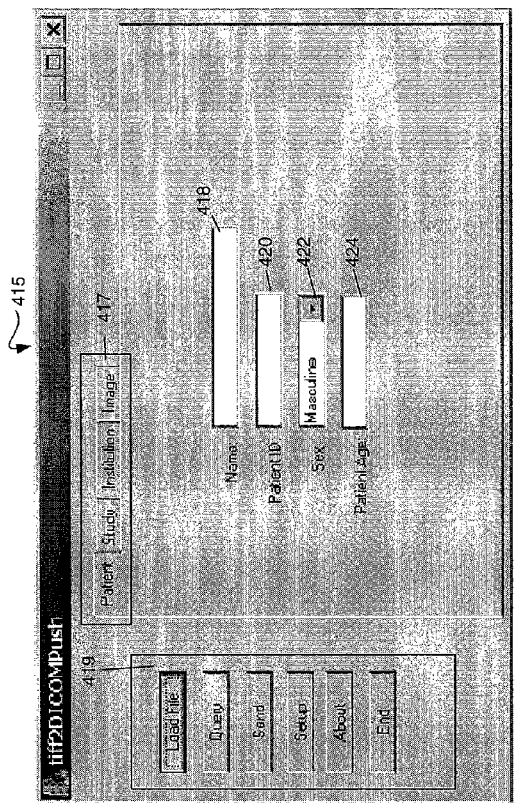
Figure 4C:
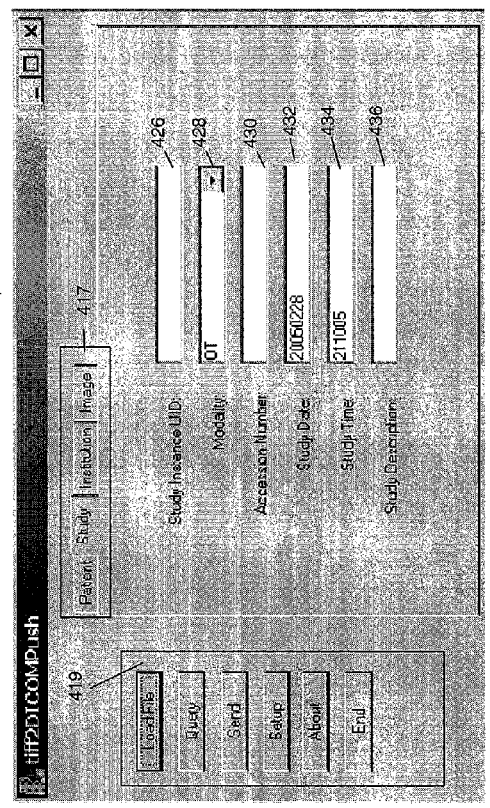
Figure 4D:
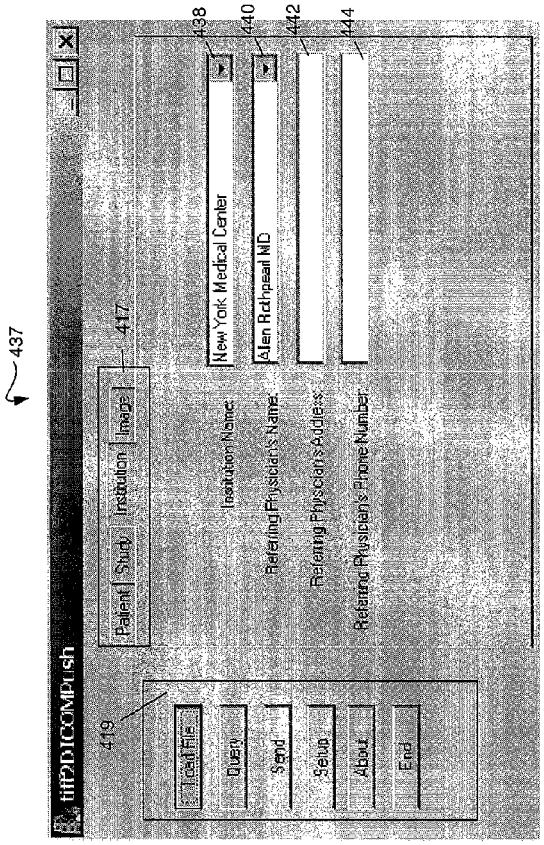

Continuing with reference to FIG. 3, DICOMPush module 304 preferably transmits images formatted as DICOM images from path name 408 to DICOM server 2. Module 304 preferably operates as a background application and is represented by an icon in the system tray. Once the icon is selected, a user interface, substantially as shown in FIGS. 4B-4D, is provided. FIGS. 4B-4E illustrate example display screens provided by module 304 that correspond to respective tabs for entering, changing and viewing information directed to a patient, study, institution and/or image, as selected in tab section 417. Also illustrated FIGS. 4B-4D is buttons section 419 that includes plurality of buttons for invoking various processes provided by module 304. For example, buttons are provided to enable a user to load a file, perform a query, send a file, setup module 304, review information regarding module 304, and terminate module 304.

FIG. 4B illustrates an example display screen 415 that is presented by module 304 and corresponds to the patient tab from tab section 417. Display screen 415 includes graphical screen controls for data entry regarding a patient, and preferably includes patient name 418, patient ID 420, gender 422 and patient age 424. Thus, users can submit various data regarding a patient via display screen 415.

FIG. 4C illustrates an example display screen 425 that is presented by module 304 and corresponds to the study tab from tab section 417. Display screen 425 includes graphical screen controls for data entry regarding a study, and preferably includes study instance UID 426, Modality 428, Accession Number 430, Study Date 432, Study Time 434 and Study Description 436. In particular, UID 426 represents a unique identifier that is used to reference a particular study. Modality 428 represents a type of equipment used to acquire a medical image of the body. For example, radiography, ultrasound and magnetic resonance imaging are examples for modalities in this context. In the example shown in FIG. 4C, modality 428 is listed as "OT," which represents "other." Study date 432, time 434 and description 436 enable a user to submit various descriptive information regarding the study associated with UID 426.

FIG. 4D illustrates an example display screen 437 that is presented by module 304 and corresponds to the institution tab from tab section 417. Display screen 437 includes graphical screen controls for data entry regarding a respective institution that provided an image corresponding with UID 426. In particular, display screen 437 includes institution name 438, referring physician's name 440, referring physician's address 442, and referring physician's telephone number 444. These data entry fields enable tracking of the institution and referring physician with regard to UID 426.

Figure 4E:
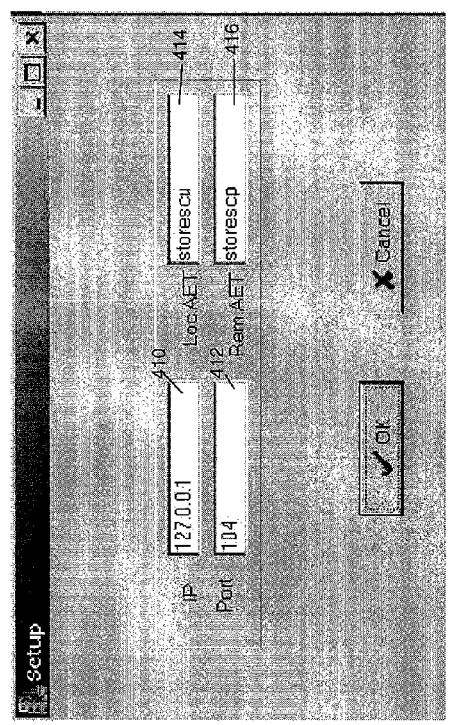

FIG. 4E illustrates an example display screen 446 that is presented by module 304 and enables a user to provide parameters used by module 304, such as described above with reference to module 302 and FIG. 4A. Display screen 446 is preferably provided when setup button is selected by a user from buttons section 417, and includes data entry controls for submitting corresponding information for Path name 408, IP address 410, Port Number 412, Local Entity Title 414 and DICOM server Entity Title 416.

Referring back to FIG. 3, another module provided in accordance with a preferred embodiment is DICOMTag2Text module 306, which is operable to provide various functionality in accordance with the teachings herein. In one embodiment, module 306 generates tagged data files that are MEDWEB compliant using data provided in an EFILM database. In an alternative embodiment, module 306 generates tagged data files that are MEDWEB compliant using data provided in an CONQUEST database. Alternatively, module 306 generates PDF fax cover pages using data provided in an EFILM database, or generates PDF fax cover pages using data provided in an CONQUEST database. In yet another alternative, module 306 generates tagged data files directly from the user's console that are MEDWEB compliant using data provided in an EFILM database. In yet another embodiment, module 306 generates tagged data files directly from the user's console that are MEDWEB compliant using data provided in an CONQUEST database, or generates PDF fax cover pages directly from the user's console using data provided in an MEDWEB tagged file.

In a preferred embodiment, the present invention provides data in a format for a database accessible by information processor 2, and not particular to CONQUEST or EFILM. By using an internal database that is continually updated via DICOM queries to the DICOM server, the overall process is streamlined by not having to transmit an entire DICOM examination to the CONQUEST or EFILM database in order to produce the PDF fax cover sheets or HTI text files. Further, by substituting repeated DICOM queries to the target DICOM server, instead of automatically transmitting the entire examination, a significant bandwidth, transmittal time, and storage space savings is produced. The query process 'asks' the target DICOM server if any new studies have arrived. If the results to the query indicates new studies, the relevant DICOM tags are pulled from the new study and added to the internal database. Thereafter, the relevant DICOM tags for the examination are transmitted instead of the entire examination, which may include hundreds of images. The inventor believes this is the most parsimonious approach toward updating the local internal database, and allows use of this single database for all relevant modules.

As used herein, the "console" refers, generally, to a command line, such as invoked from the MICROSOFT WINDOWS command prompt, also known in the industry as a "C prompt." One skilled in the art will recognize that the letter C can be substituted for any other respective drive letter, and that any operating system, such as UNIX, which provides a prompt for command line execution is applicable herein.

In a preferred embodiment, tagged file formats and Acrobat PDF Fax Cover files are provided according to predetermined specifications that correspond with the particular format for the data. For example, one type of query may be provided for EFILM data files, and another type of query may be provided for CONQUEST data files. Preferably, queries are formatted for a database maintained by information processor 2, such as a MICROSOFT ACCESS or other SQL compliant database.

Figure 4F:
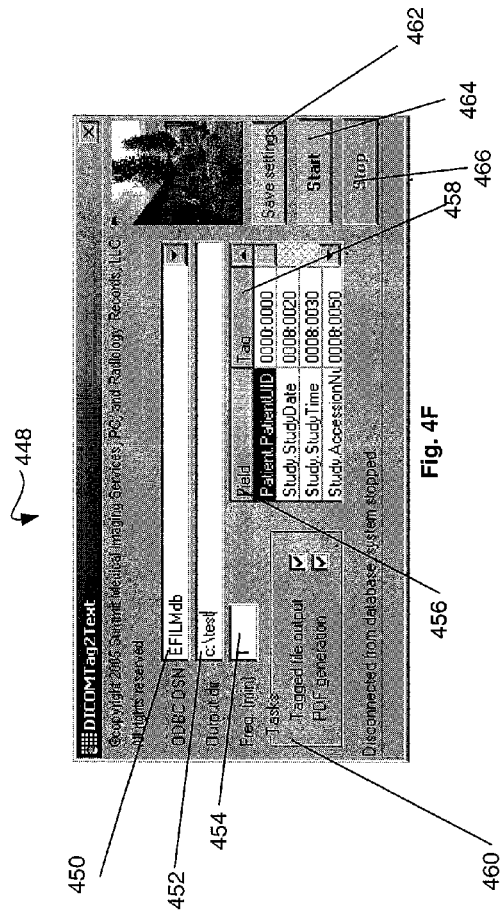

FIG. 4F illustrates an example display screen 448 that is preferably provided by module 306 and provides various configuration settings. As shown in FIG. 4F, ODBC DSN 450 identifies open database connectivity ("ODBC") data source names. ODBC-DSN 450 indicates an alias defined by an ODBC data source administrator. For example, "CONQUESTdb" is typically defined for a CONQUEST data base EFILMdb is typically defined for an EFILM Access database. Output dir. 452 identifies a file directory where output files are placed. Freq. (min) 454 represents the frequency in minutes to poll the database for new records.

Continuing with reference to FIG. 4F, Fields 456 and Tags 458 are provided in an editable grid, where Fields 456 represents a database field name, and Tags 458 represents the corresponding tag to be used. In a preferred embodiment, database field names use SQL-like syntaxes. For example, TableName.FieldName. (i.e., Patient.PatientID) indicates the data field PatientID defined in a database table, "Patient." Tasks control panel 460 contains two checkboxes, the first ("Tagged File Output") selects output to tagged files and the second ("PDF Generation") selects output to PDF files. Additionally, save settings button 462, when selected, saves the current settings. Start button 464, when selected, preferably causes information processor 2 to start execution of DICOMTag2Text module 306 using the respective values defined in display screen 448. Stop button 466, when selected, preferably halts execution of DICOMTag2Text module 306. All graphic user interface settings are persistent in disk, such that closing module 306 does not result in the loss of the values. When module 306 executes in the future, the settings are loaded automatically. In addition to graphic screen controls, display screen 448 preferably provides status information, such as displayed in FIG. 4F at the bottom of display screen.

In a preferred embodiment of the present invention, selecting the cross icon in the upper right corner of display screen 448 does not result in termination of the module 306. Instead, selecting the cross icon merely minimizes the window to the system tray near the clock. In order to close terminate module 306, the user preferably selects (e.g., "right clicks") on the tray icon and a pop-up menu is shown, such as illustrated in FIG. 4G.

Figure 4G:
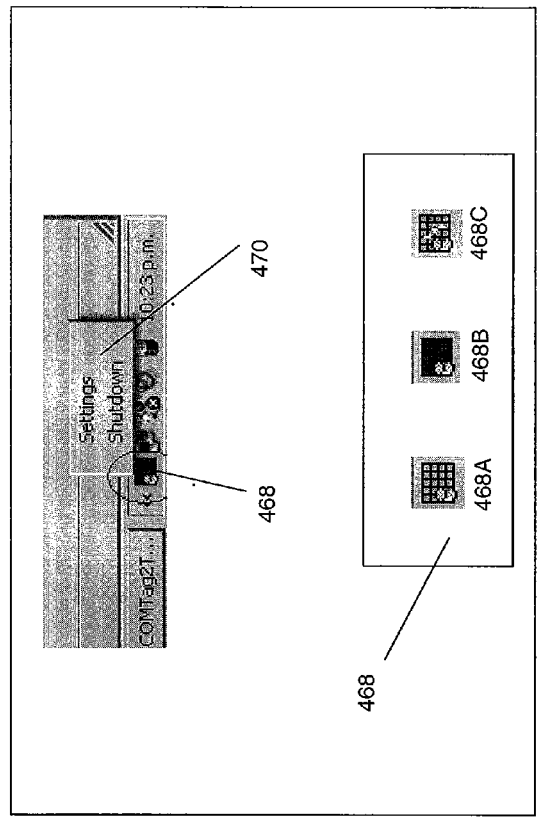

FIG. 4G illustrates a MICROSOFT WINDOWS "tray icon" 468 that is preferably selected to control operation of module 306. When a user selects tray icon 468, pop-up menu 470 is preferably presented, enabling the user to select a choice to terminate module 306. Continuing with reference to FIG. 4G, icons 468A, 468B and 468C represent different states of icon 468, which represent the status of module 306. For example, icon 468A indicates that Start button 464 has been selected and module 306 is operating. Icon 468B indicates that Stop button 466 has been selected and that module 306 has stopped. Further, icon 468C indicates that module 306 is currently executing a task.

As noted above, the present invention is operable by executing "console" commands at a command line prompt. The following are example parameters that are meaningful when invoking module 302 via the console. In a preferred embodiment, one parameter is used at a time. In a preferred embodiment, all of the parameters submitted via the graphic user interface, such as illustrated in FIGS. 4A-4K, can be defined and applied while operating module 306 from the console.

Figure 4H:
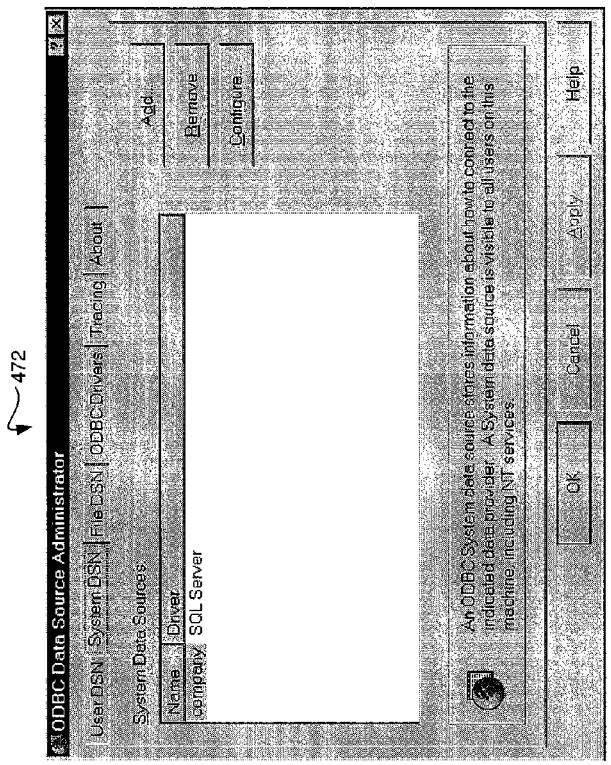
Figure 4I:
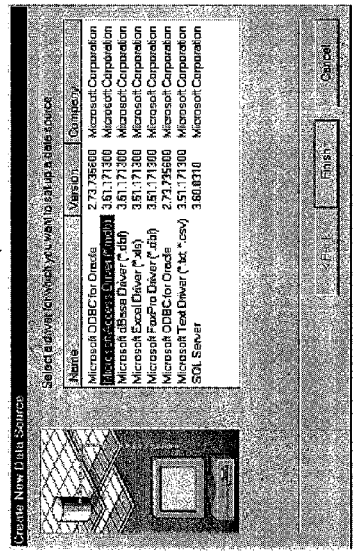

FIGS. 4H and 4I illustrate example MICROSOFT WINDOWS display screens for use in configuring a Microsoft ODBC data source. As known to those skilled in the art, a user configures a DSN by selecting the System DSN tab (display screen 472) and adding a name and driver. Thereafter, a new data source is added (display screen 474) by selecting a respective driver. Thus, as known to those skilled in the art, the present invention preferably avails ODBC to provide transmission of data between a plurality of respective data sources.

Figure 6A:
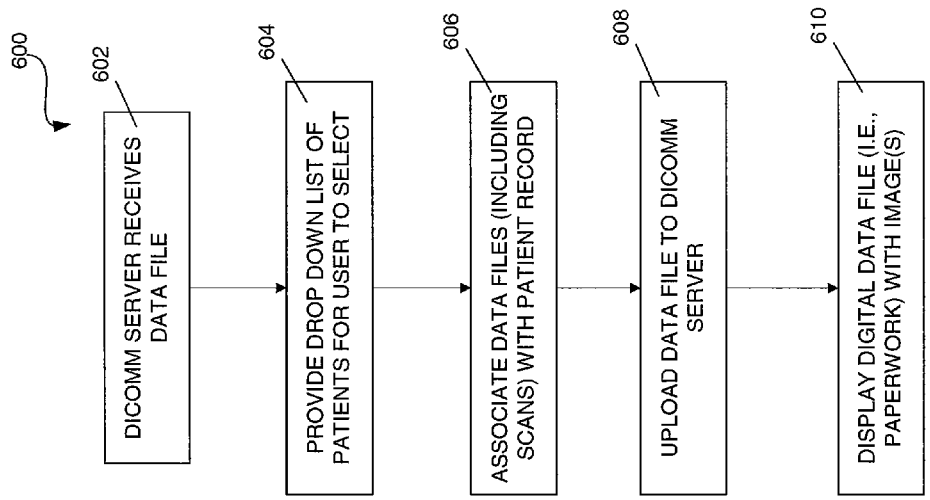
FIG. 6A is a flow chart that illustrates steps associated with processing a file in accordance with the DICOMadder module of the present invention.

Referring back to FIG. 3, the present invention further includes DICOMadder module 308 that preferably reads demographic patient information from a data file. FIG. 6A is a flow chart that illustrates steps 600 associated with processing a file in accordance with module 308. At step 602, a data file becomes available to module 308 after a patient examination is acquired by a DICOM server 2. The data file preferably includes information regarding the patient, along with detailed information on the examination itself. Module 308 reads this file either directly from an ftp folder or a local folder. Module 308 then provides a pull down menu for the user containing a patient list (step 604). Any paper that is scanned, for example, via a sheet fed or auto-feed TWAIN scanner, is preferably associated with a particular patient examination by module 308 (step 606). Module 308, thereafter, automatically uploads the data file to the DICOM server as part of the imaging examination (step 608). At step 610, the examination is available for viewing, for example by a radiologist for interpretation, and the clinical patient paperwork displays simultaneously as a separate DICOM series. In this way, the present invention allows for the viewing of patient information at the same time as digital images.

In a preferred embodiment, each feature available via DICOMadder module 308 preferably performs one or more functions related to the task of attaching non-DICOM paperwork/clinical data to a DICOM examination. Some can be run concurrently with each other. Others have special functions such as allowing entry of certain DICOM tags as part of the conversion, or allow e-mail attachments in TIFF/JPEG format to automatically convert itself to DICOM format. Using various combinations of these utilities and applications allows for different hardware and software configurations to carry out the process of adding non-digital patient data directly to specific DICOM image examinations.

One feature associated with DICOMadder module 308 uses JPEG files from a twain scanner, fax transmission, email attachments or JPEG print drivers, and attaches the converted DICOM file to the appropriate DICOM examination. DICOMfaxadder module 310, described below, automatically attaches faxed paperwork to a DICOM examination. Further, a DICOMadder module 308 software library is DICOMtags2txt. This application produces the required patient data file for the DICOMadder and produces the cover sheet for the DICOMfaxadder application. DICOMTag2Text module 306 allows the use of EFILM, CONQUEST DICOM or other database servers to be used to produce demographics and other materials required by DICOMadder module 308 and DICOMfaxadder module 310, in order to make the demographics and materials universally compatible with any commercially available DICOM server.

Other modules (or utilities) provided via DICOMadder module 308 run concurrently, or separately from DICOMadder module 308 and DICOMfaxadder module 310 and DICOMTag2Text module 306. These utilities do ancillary jobs such as auto-uploading data to DICOM server 2, acting as file daemons to monitor folders for new data, and automatically processing or uploading the data for conversion of TIFF or JPEG format scanned files to DICOM files. The utilities also allow the addition of referring physician information (address, phone, fax) to the DICOM examination if these data are lacking, and is meant to be used by administrative personnel to add this information to the DICOM file if it is missing from the original DICOM worklist. Using various custom combinations of these utilities and applications, allows for different hardware and software DICOM server configurations to carry out the process of adding non-digital patient data directly to specific DICOM image examinations.

Thus, DICOMadder module 308 reads certain demographic patient information from a data file. This data file becomes available to the DICOMadder module 308 as soon as a patient examination is acquired by a DICOM server 2. The data file includes information on the patient, along with detailed information on the examination itself. The DICOMadder can read this file either directly from an ftp folder or a local folder. It then provides a pull down menu for the user containing a patient list, and allows papers scanned from a sheet fed or auto-feed TWAIN scanner to be associated with a particular patient examination, and automatically uploaded to the DICOM server as part of the imaging examination. The end result is when the examination is opened by the radiologist for interpretation, the clinical patient paperwork displays simultaneously as a separate DICOM series, allowing the viewing of patient information at the same time as the digital images.

Figure 6B:
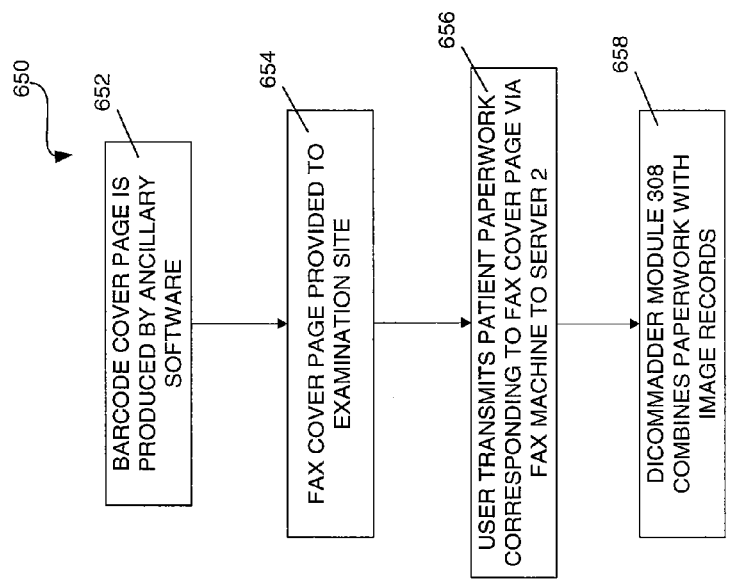
FIG. 6B is a flow chart illustrated that illustrates steps associated with the workflow in accordance with DICOMfaxadder module of the present invention.

Also referring to FIG. 3, the present invention preferably provides DICOMfaxadder module 310 that enables direct or remote scanning of non-digital paper-based patient data directly into DICOM imaging examinations. In a preferred embodiment, fax server 2 receives fax cover pages that are generated with a barcode. The fax is processed by our software in a similar way as scanned paperwork is processed by the DICOMadder module 310. FIG. 6B is a flow chart illustrated that illustrates steps 650 associated with the workflow in accordance with module 310. At step 652, the facsimile cover page comprising a bar code is produced by ancillary software. The fax cover page containing the bar code is then either automatically uploaded to an FTP server 2 for download by the remote examination site personnel, automatically printed at the examination site via a remote internet printing application, or automatically faxed to the examination site directly (step 654). A technologist at the remote examination site then uses the fax cover sheet to transmit corresponding patient paperwork via a simple fax machine to server 2 (step 656). The end result is that users can fax the patient paperwork directly into the patients DICOM examination. This application obviates the need for paper scanners and capture programs, and greatly simplifies the addition of non-digital handwritten patient information to the DICOM examination (step 658).

In accordance with a preferred embodiment, another module, DICOMProxy module 312, is provided that functions in conjunction with a DICOM Storage SCP, receives an image via a DICOM communication, modifies the DICOM tags for the examination following various criteria, and then forwards the modified examination to one or more servers. Detailed discussions regarding routing rules and replacement rules in accordance preferred embodiments is described below with reference to FIGS. 5A-5G.

Figure 4J:
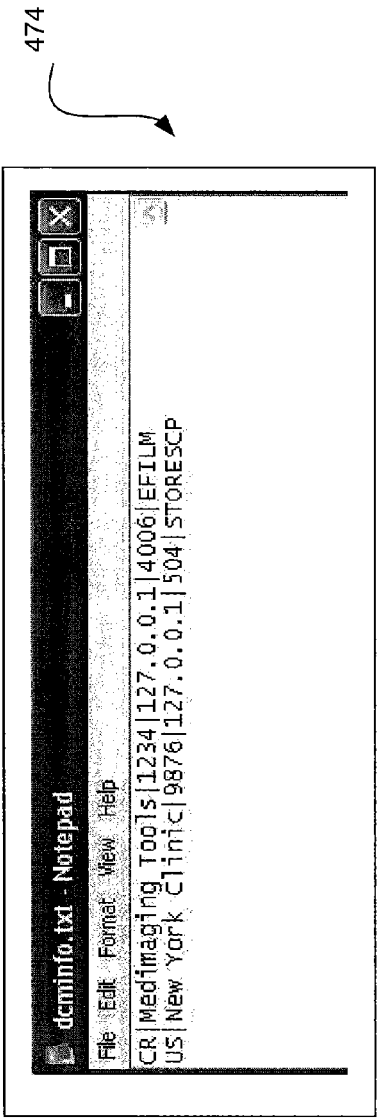

FIG. 4J illustrates an example text file 474 (labeled "dcminfo.txt") that is referenced in one embodiment by DICOMProxy module 312 for supplying parameters to DICOMProxy module 312 in the event that various DICOM tags are not provided in the DICOM image, or need to be changed. As shown in FIG. 4J values are provided for DICOMProxy module 312. In the example text file 474 shown in FIG. 4J, the values are delimited, such as by the "pipe" (|) character. The values in FIG. 4J represent the following: 'CR' is a character string to be matched in the DICOM tag 'institution name', 'Medimaging Tools' is the new institution name to be entered in the institution name tag in the event of a match, '1234' is the prefix for the accession number tag to be added to the accession number field, '127.0.0.1' is the IP address of the DICOM server to forward the examination to following the changes, '4006' is the port number corresponding to the IP address, and 'EFILM' is the title of the DICOM server. Continuing with this example, the last three fields are address info of where to send the examination in the event of a 'CR' match, after the tag transformations are made.

Figure 4K:
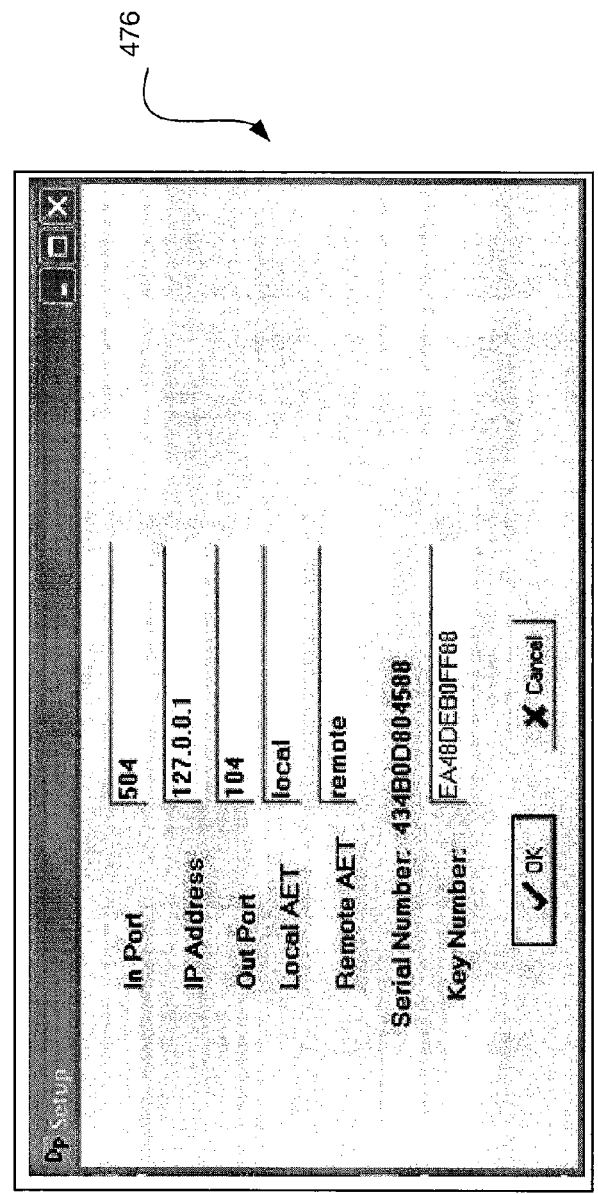

FIG. 4K illustrates an example DICOMProxy module setup display screen 476 that preferably uses values provided by either the DICOM image file or the text file 474 to define parameters used by DICOMProxy module 312. As shown in setup display screen 476, various parameters can be defined, including Port (the DICOM Storage SCP port), IP Address (the IP address of the DICOM Server), Out Port (the Port number of the DICOM Server), Local AET (Entity Title of this application), Remote AET (Entity Title of the DICOM Server), and Key number (a security key provided by the software provider after a valid serial number is transmitted.

Figure 5A:
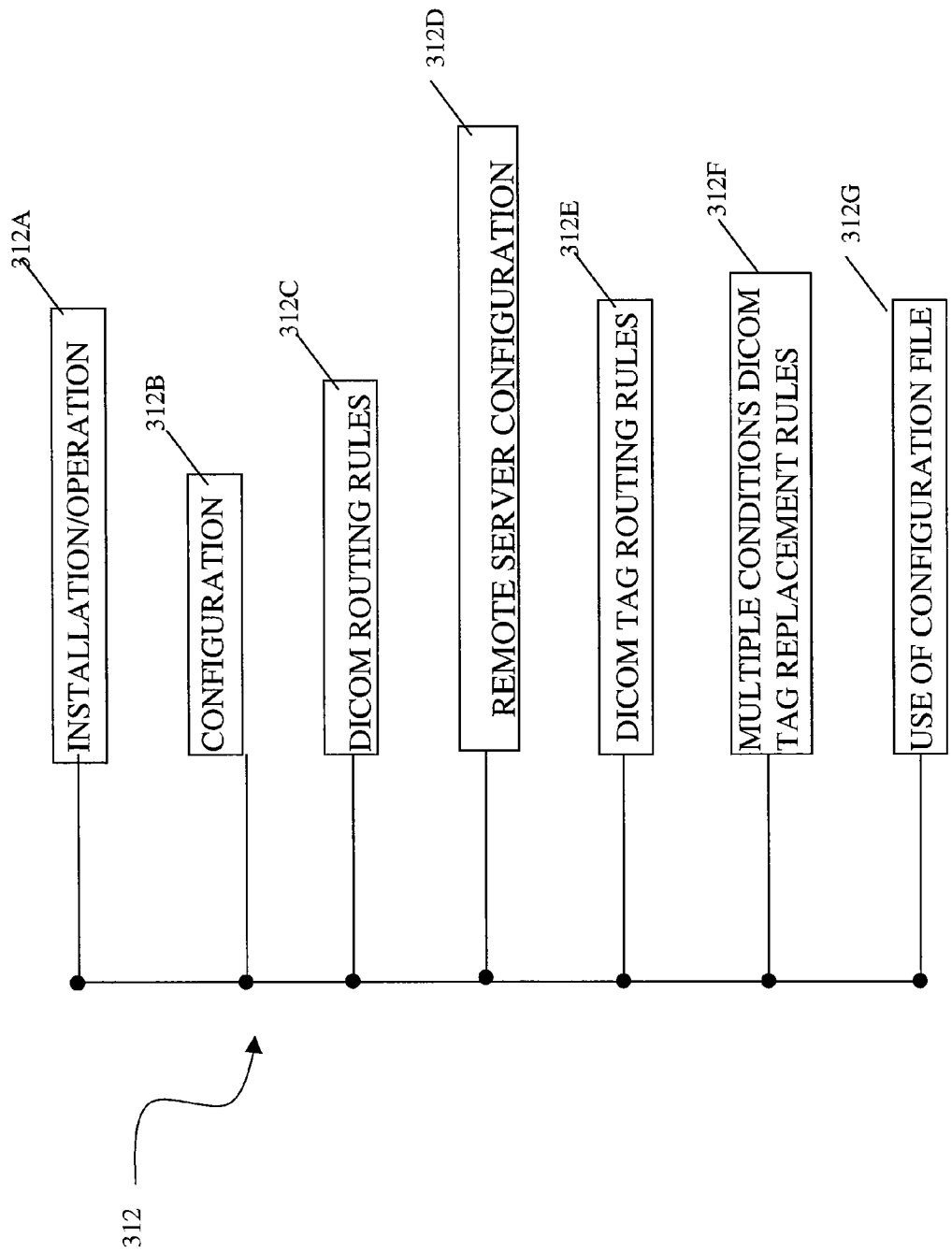
FIG. 5A is a block diagram that illustrates elements of an alternative and preferred embodiment of DICOMProxy module.

FIG. 5A is a block diagram that illustrates elements of an alternative and preferred embodiment of DICOMProxy module 312. Preferably, DICOMProxy module 312 includes submodules 312A-312G that collectively provide extended functionality over the prior art. F or example, installation/operation submodule 312A enables a user to configure and setup DICOMProxy module 312, as well as to view operating status information regarding DICOMProxy module 312.

Figure 5C:
FIG. 5C is an example display screen showing a WINDOWS SYSTEM TRAY and illustrating an active session of the DICOMProxy module in accordance with an example embodiment.
Figure 5B:
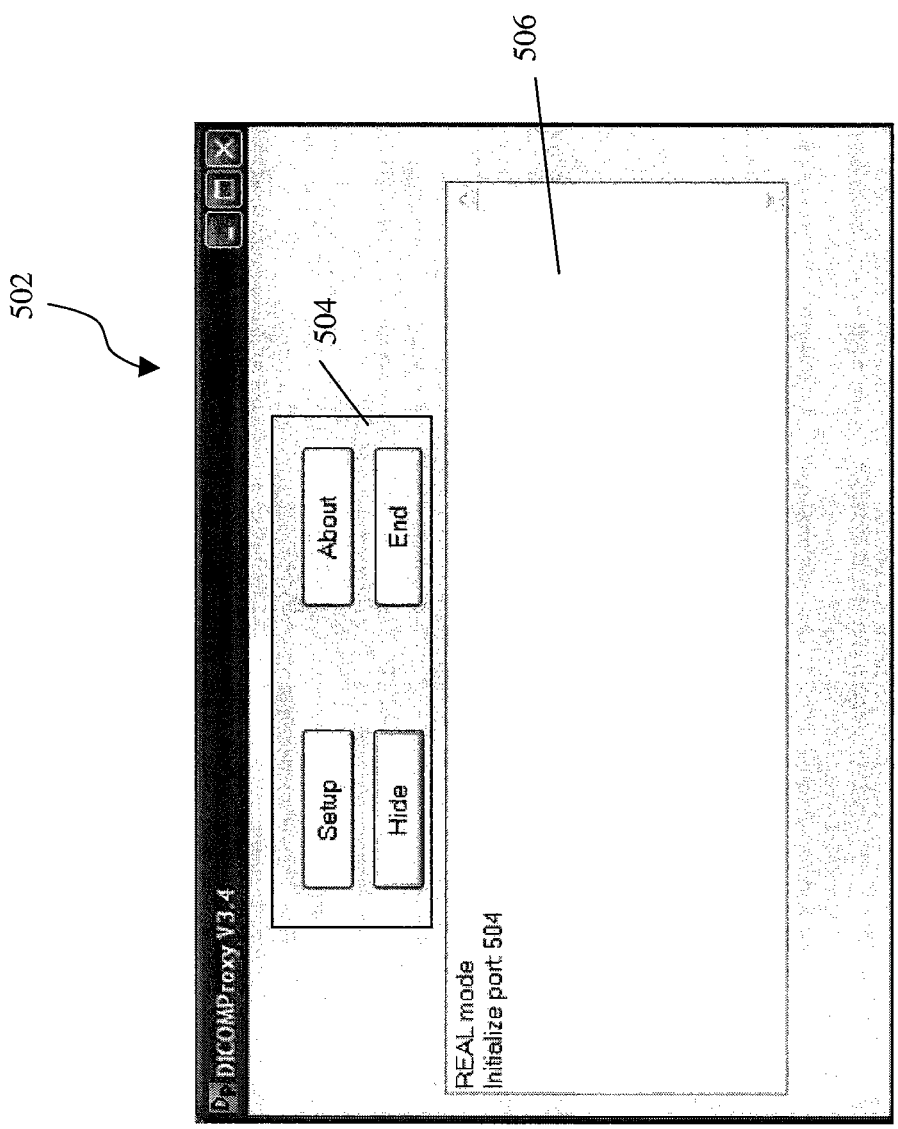
FIG. 5B illustrates an example DICOMProxy module configuration display screen in accordance with an example embodiment.
Figure 5D:
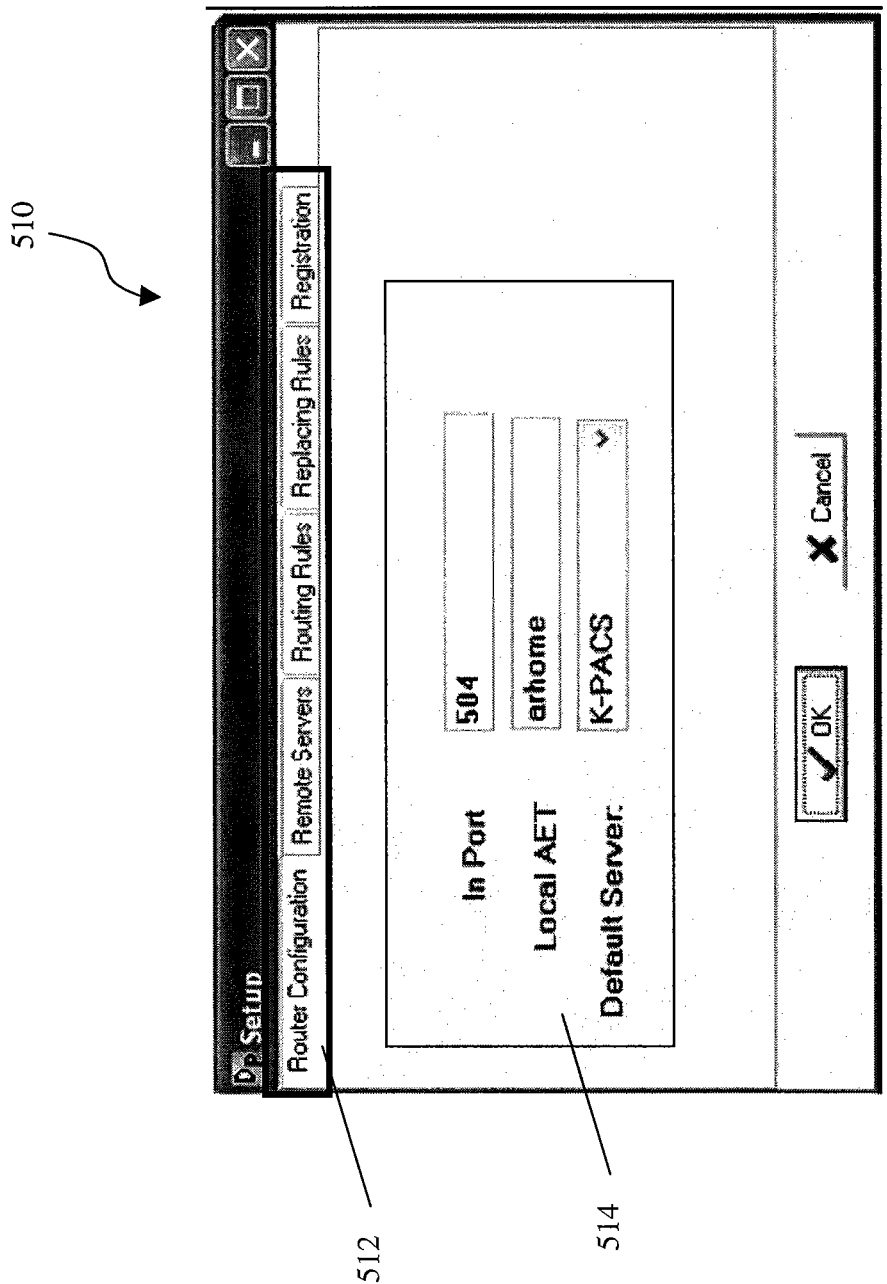
FIGS. 5D-5G illustrate example display screens for configuring and using the DICOMProxy module for various functionality in accordance with a preferred embodiment.

FIG. 5B illustrates an example DICOMProxy module configuration display screen 502 that corresponds with configuration 312B and is preferably provided to a user to review and configure settings for DICOMProxy module 312. Preferably, DICOMProxy module 312 is installed as an executable application in a dedicated folder on the user's local workstation drive. Further and in a preferred embodiment, DICOMProxy module 312 operates as a background application following installation and remains active in the WINDOWS system tray 408, as shown in FIG. 5C. In this embodiment, a user configures DICOMProxy module 312 by selecting an icon representing DICOMProxy module 312 in system tray 508 and, in response, display screen 502 is provided. Controls are preferably provided in control section 504 to enable a user to setup DICOMProxy module 312, hide DICOMProxy module 312 (i.e., by minimizing display screen 502 to the system tray 508), to end the DICOMProxy module 312 session and to receive information about DICOMProxy module 312. Selecting the End button preferably closes the DICOMProxy module 312 and removes the program from the system tray 508. In the example shown in FIG. 5B, the value "Real Mode" is displayed to indicate that a code number or other form of authorization has been provided (for example, following registration payment) to a user and entered. Further, a port number is preferably shown as initialized to indicate that a port is open and taken over by DICOMProxy module 312. In case the respective port is being used by another service, process or application, an error is preferably displayed, such as "Error: Cannot Initialize Port." FIG. 5D illustrates an example display screen 510 that includes graphical screen controls, including tab and textbox controls, for selecting and defining various features of DICOMProxy module 312 and corresponds with DICOM Routing Rules 312C (FIG. 5A). In example display screen 510, tab control section 512 includes selectable controls for a user to define selections for router configuration, remote server(s) configuration, router rules, data replacement rules and user registration.

Continuing with reference to FIG. 5D, router configuration section 514 includes three data entry fields to configure a router associated with DICOMProxy module 312. In particular, a textbox control "In Port" is provided to define the DICOM Storage SCP port assigned to DICOMProxy module 312. Further, "Local AET" textbox control is operable to define the Application Entity Title assigned to DICOMProxy module 312. Moreover, "Default Server" textbox control is operable to define the server used by DICOMProxy module 312 in the event no matching routing conditions are met. In a preferred embodiment, DICOMProxy module 312 is capable of receiving images in the various DICOM formats, including: JPEG lossless (Transfer Syntax="1.2.840.10008.1.2.4.70"), Explicit VR Little Endian (Transfer Syntax "1.2.840.10008.1.2.1"), Implicit VR Little Endian (Transfer Syntax="1.2.840.10008.1.2") and JPEG lossy (Transfer Syntax="1.2.840.10008.1.2.4.50"). Preferably, DICOMProxy module 312 sends the image with the same Transfer Syntax that the image was received in.

Figure 5E:
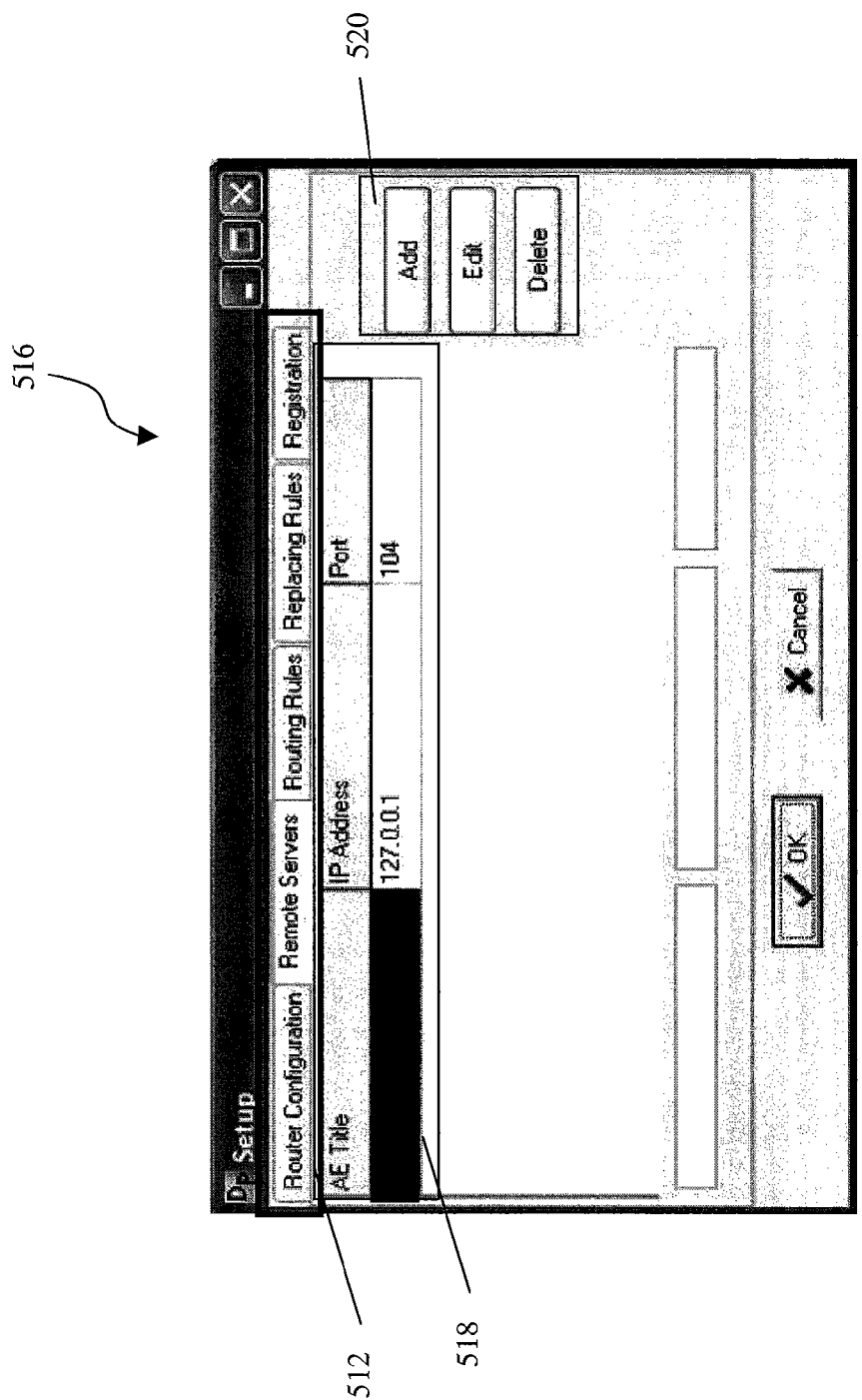

FIG. 5E illustrates an example display screen 516 that corresponds with Remote Server Configuration 312D (FIG. 5A). Display screen 516 preferably includes remote servers table 518 that includes textbox controls for a user to define any number of remote servers. For each remote server, three parameters are specified: AET (representing the Application Entity Title of a remote server), IP Address of the remote server and Port number of a respective service running on the remote server. Button control section 520 includes graphical screen controls for adding, editing and deleting entries in the table corresponding with the respective display screen. In the example shown in FIG. 5E, section 520 enables a user to add, edit or delete remote servers. Of course, one skilled in the art will recognize that various other graphical screen controls may be provided, such as Up and Down buttons that, when selected, change the position of a selected rule.

Figure 5F:
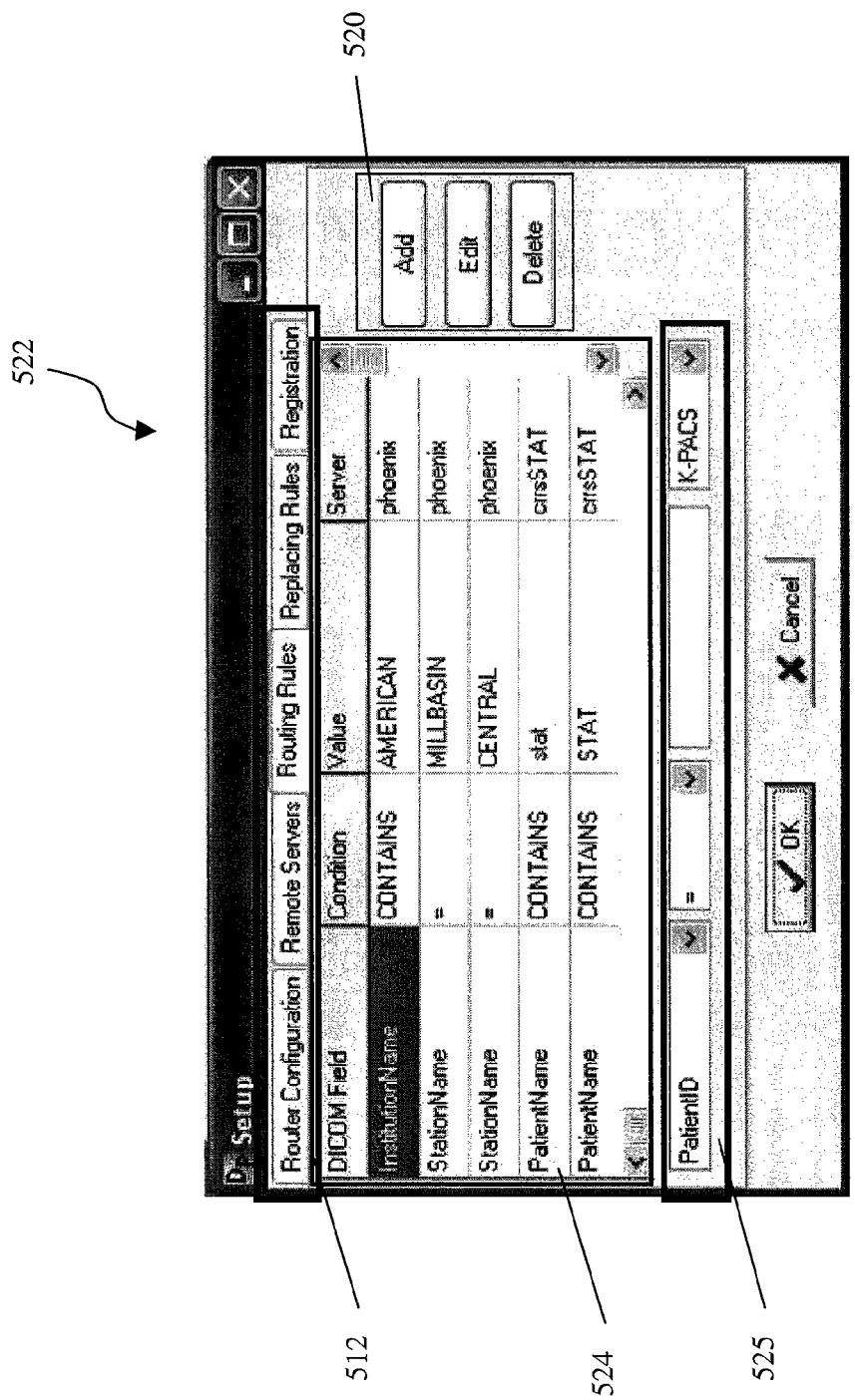

The remote servers are referenced by their respective AET's, such as for defining routing rules, as shown in FIG. 5F. FIG. 5F illustrates an example display screen 522 that corresponds with DICOM Routing Rules 312E (FIG. 5A). Routing rules enable a user to define particular servers and/or respective services that are to receive a DICOM image file in case one or more conditions are met. Using the controls provided in section 520 of display screen 522, rules can be added, deleted, or edited. In the context of display screen 522, the Add button is selected to add a new rule, the Edit button is selected to modify a selected rule and the Delete button is selected to delete a selected rule. As shown in the example display screen 522, routing rules condition table 524 is provided to enable a user to enter values that represent a DICOM data field, a respective condition, a respective value and a service (or service) that is to receive the DICOM image file in case the field, condition, and value is met. If, for any reason a selected remote DICOM server is unavailable and transmission fails, DICOMProxy module 312 preferably saves the DICOM image file in a local folder named for the AET of the remote server for which the images were intended.

In a preferred embodiment, the DICOM field value provided in table 524 is entered by the user via a pull-down menu. The available DICOM fields available on the pull-down menu include: PatientID, PatientName, PatientBirthDate, PatientSex, StudyDate, StudyTime, StudyID, Modality, AccessionNumber, StudyDescription, BodyPart, InstitutionName, StationName, RefPhysiciansName, RefPhysicianAddress, and RefPhysicianPhone. Conditions can be defined for any of these fields. The operators available on the pull-down menu to define test conditions and include: "=" (representing "is equal to"), "CONTAINS" (representing "contains the string"), "< >" (representing "is different than"), ">=" (representing "is equal or more than"), and "<=" (representing "is equal or less than"). The Value data are entered directly into this field by the user. Finally, the Server field is chosen via a pull-down menu, and the available server options correspond to those entered in the remote servers section 518, as displayed in FIG. 5E, of DICOMProxy module 312.

In a preferred embodiment, and in the event a DICOM association (as known in the art) cannot be made for a particular examination, or fails for some reason, DICOMProxy module 312 preferably saves the DICOM image file representing an examination in a local folder for safekeeping. Preferably, the file is saved with the same name as the remote server AET that transmitted the image file. Moreover, DICOMProxy module 312 preferably regularly attempts, such as every 20 minutes, to retransmit any examinations not successfully sent. In case the image file is successfully transmitted, DICOMProxy module 312 preferably moves the image file to a folder named "sent." Also in a preferred embodiment, DICOM image files are deleted from all local folders after expiration of one week, regardless of whether a respective DICOM image file was successfully sent.

In addition to sections 520 and 524, additional conditions can be defined in section 525. In accordance with a preferred embodiment, section 525 is used to produce rules by the user and via pull down menus. Preferably, the first pull down contains the DICOM tags or fields to be examined, the second pull-down contains the condition to be used (e.g., CONTAINS, =, or the like) the third column contains an alphanumeric character(s), numeric constant or value, or a blank, and represents the condition to be satisfied. The fourth column preferably the DICOM field to be modified or replaced when the conditions in the first three columns are satisfied, and a fifth column may further be provided that represents another DICOM tag or field, alphanumeric value or numeric constant that to be put into the value of the first column when the conditions are satisfied.

Figure 5G:
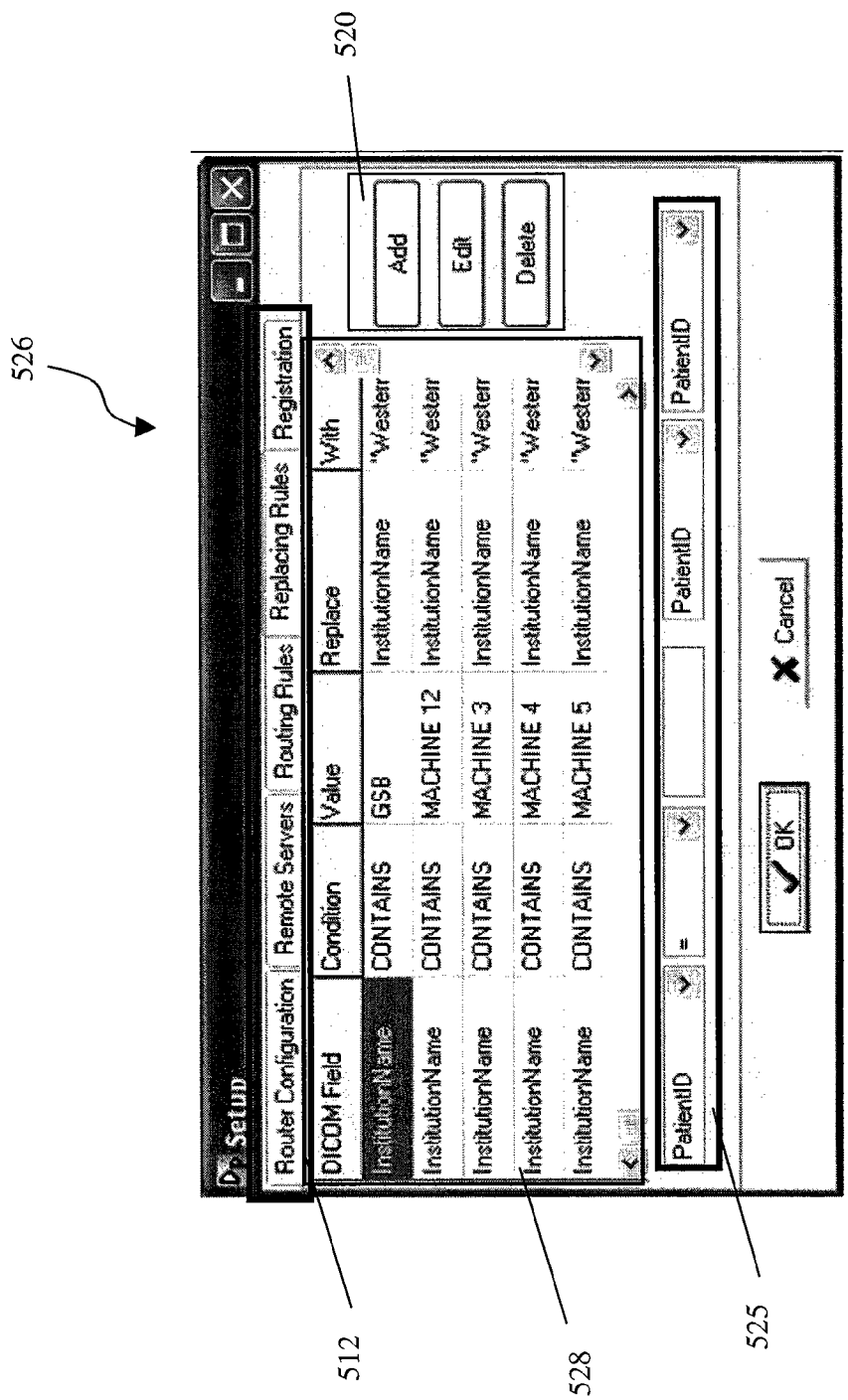

FIG. 5G illustrates an example display screen 526 that corresponds with Multiple Conditions DICOM Tag Replacement Rules 312F (FIG. 5A). By defining replacement rules, users can ensure that data that are entered incorrectly, inaccurately, are improperly formatted or the like can be replaced with data that are proper. Using the controls in display screen 526, rules can be added, deleted, or edited (section 520). Also as shown in example display screen 526, replacement rules condition table 528 is provided for a user to define replacement rules, and includes a selection for a DICOM field that is entered by the user via a pull-down menu. Preferably, the available DICOM fields available on the pull-down menu include: PatientID, PatientName, PatientBirthDate, PatientSex, StudyDate, StudyTime, StudyID, Modality, AccessionNumber, StudyDescription, BodyPart, InstitutionName, StationName, RefPhysiciansName, RefPhysicianAddress and RefPhysicianPhone. Preferably, DICOMProxy module 312 performs error checking check a DICOM Tag in the "With" column to be sure that the data are of a compatible data type before allowing its use. For example, DICOMProxy module 312 does not allow the value in StudyDate to be replaced with the value in PatientID. In this way, field data type integrity is ensured.

Continuing with reference to display screen 526 shown in FIG. 5G, operators are available in table 528 and are preferably available via a pull-down menu to define test conditions. The conditions preferably include: "=" (representing "is equal to"), "CONTAINS" (representing "contains the string"), "< >" (representing "is different than"), ">=" (representing "is equal or more than"), and "<=" (representing "is equal or less than"). The Value field is preferably entered directly by the user as an alphanumeric value or a DICOM tag. The Replace field allows selection of a respective DICOM field to be replaced if a condition is true, and the With field, which is preferably entered by the user as a alphanumeric value or a DICOM tag, is used to substitute the value in the defined DICOM field of the respective row in table 528. Thus, if a rule is valid (true), DICOMProxy module 312 replaces the DICOM Tag specified in the "Replace" column with another DICOM Tag, or alphanumeric Value in "With" column entered by the user.

Referring back to FIG. 5A, use of a configuration file 312G preferably enables a user to define multiple conditions that produce multiple modifications and which can be set by rules provided (e.g., scripted) in a configuration text file, such as named "multiple.txt." Of course, one skilled in the art will recognize that data files of other formats, including spreadsheet files, single file or relational database files, image files, XML files, streaming data, etc., can be used to provide configuration information for DICOMProxy module 312. When a multiple conditions configuration text file is used, the configuration text file is preferably stored in the same directory as the DICOMProxy module 312. In one embodiment, a general format for defining the rules is as follows: Condition1&Condition2& . . . &ConditionN: Replace1&Replace2& . . . &ReplaceM In accordance with the above, each Condition is preferably formed as: DICOMFIELD|Condition|Value, and each Replace is in the form: DICOMFIELD|Value For separating Conditions from Replacements a colon (":") or other character may be used. The following examples illustrate two formats that are useable for replacement rules in a text file:

InstitutionName|CONTAINS|RADIOLOGY&Modality|=|CT:RefPhysician|"John^Smith"

The above example enables DICOMProxy module 312 to replace all instances of the referring physician tag with "John Smith," providing the image has an institution name tag that contains the characters "RADIOLOGY" and has a modality tag of 'CT'

EXAMPLE 2

PatientName|CONTAINS|CR&PatientBD|<=|20000101: StationName|"Pediatrician"

The above example enables DICOMProxy module 312 to replace the StationName tag value with the string "Pediatrician," providing the image has a patient name tag that contains the alphanumeric string "CR" and the PatientBD tag is less than or equal to Jan. 1, 2000.

The valid DICOM Fields for use with the multiple conditions text file option are: PatientID, PatientName, PatientBirthDate, PatientSex, StudyDate, StudyTime, StudyID, Modality, AccessionNumber, StudyDescription, BodyPart, InstitutionName, StationName, RefPhysiciansName, RefPhysicianAddress, RefPhysicianPhone, WWIDTH, WCENTER, TR, TE, and FLIP.

Some special advanced uses of DICOMProxy module 312 are available by using the configuration file. For example, automatic window and leveling in real time is supported, as well as adding a prefix for an accession number or other DICOM field, in accordance with a preferred embodiment. Certain older MRI and CT units send images with arbitrarily different window/level values even within a particular series of images. The multiple.txt option can be used for changing window/level values, using either fixed values or automatic calculated values based on the image histogram. An example of a multiple.txt text data file employing this functionality is as follows:

InstitutionName|CONTAINS|AMERICAN&Modality|=|MR:WWIDTH|"440"&WCENTER|"AutoWL".

The Automatic window/level ("AutoWL") option in the above example enables DICOMProxy module 312 to perform selected statistics on the image histogram, and to calculate the average pixel value and standard deviation. From these values, DICOMProxy module 312 preferably derives an optimum window width and center position for each image. Use of this option is preferably should used with servers or computing devices equipped with high-speed processors and sufficient memory, otherwise a speed degradation may become apparent because the computed statistics on every image is processor and memory intensive.

It is also possible to specify a specific window/level for each image using absolute values, or values of TR and TE. This allows assigning specific W/L values for T1 and T2 weighted images:

TR|IN|200,700&TE|IN|10,100&FLIP|=|90: WWIDTH|"500"&WCENTER|"800".

For limiting to a particular institution, add another condition:

TR|IN|200,700&TE|IN|10, 100&FLIP|=|90&InstitutionName|CONTAINS|Western: WWI DTH|"500"&WCENTER|"800".

Another feature of using a configuration file includes adding a prefix for accession number or other DICOM field. For some teleradiology applications, particularly those used in various areas of the US government, sending sites are identified by a 3 digit sending site code. This is basically a shorthand way of identifying a particular institution name, or a sub-institution within a larger one. This three digit code can be used to limit access to the database by a user to only certain patients, and is added as a prefix to the accession number followed by a "#." For a sending site institution name of APEX RADIOLOGY identified by a sending site code of '440' the syntax would be:

InstitutionName|CONTAINS|APEX RADIOLOGY: AccessionNumber|"440#"+AccessionNumber

Thus, using a configuration text file is particularly useful to automate various processes, such as to modify data provided in one or more DICOM tags.

Preferably, the present invention comprises various other modules, which can run concurrently, or separately from DICOMadder module 308. These ancillary modules do the jobs of auto-uploading to the DICOM server 2, watching folders for new data to be automatically processed and uploaded, and converting TIFF or JPEG format scanned files to DICOM files which can then be processed by the DICOMadder application or one of the other applications in the library, substantially as described herein. Ancillary software also allows the addition of referring physician information (address, phone, and fax) to the DICOM examination if these data are lacking, and is meant to be used by administrative to add this information to the DICOM file if it is missing from the original worklist.

Other ancillary applications in the DICOMadder library produce the patient data file for the DICOMadder module 308 and produces the cover sheet for the DICOMfaxadder module 310. Although some DICOM server produces this file automatically (i.e. MEDWEB), other DICOM servers do not. The present invention preferably provides EFILM and CONQUEST DICOM servers to be used to produce similar demographics, so that DICOMadder module 308 and DICOMfaxadder module 310 can be universally used with any commercially available DICOM server.

Features of DICOMfaxadder module 310 is provided below with reference to FIG. 7 and in reference to an embodiment of the present invention.

Figure 7:
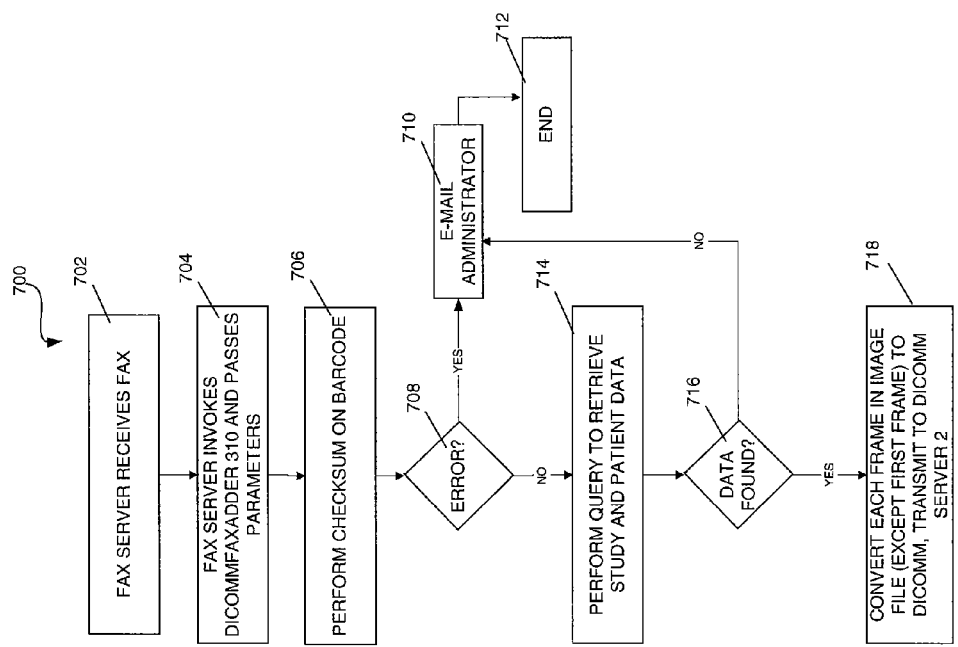
FIG. 7 is a flow chart illustrating steps associated with processing a facsimile that is received by a fax server in accordance with the present invention.

FIG. 7 is a flow chart illustrating steps 700 associated with processing a facsimile that is received by Fax server 2. At step 702, a new FAX arrives the Fax server 2. Thereafter, Fax server 2 invokes DICOMFaxAdder module 310 and passes parameters thereto, including, for example, path, folder, base name and barcode. In a preferred embodiment, the barcode is formatted to include PatientUID-PatientID. A checksum process is performed on the bar code that is received to verify that no error has occurred during transmission. In step 708, a determination is made to determine whether an e-mail exists. If so, the process branches to step 710, and an e-mail is preferably sent to a system administrator alerting him/her of the error. Thereafter, the process terminates (step 712). Alternatively, if at step 708, it is determined that no error has occurred, then, at step 714, a query is performed, for example, to an EFILM database to retrieve corresponding study and patient tables. If after a determination in step 716 that no data can be retrieved regarding, for example, the respective PatientUID, the process branches to step 710 and an error e-mail is sent to system admin, and no further processing is done (step 712). Alternatively, if data are returned from the query, then the information retrieved from the database each frame in a corresponding TIFF file, except the first one (representing the FAX cover), is converted into a DICOM image and sent to DICOM Server 2 (step 718).

In a preferred embodiment, DICOMFaxAdder module 308 is a command line (console) application that is called by the fax server 2 application programming interface ("API"). DICOMFaxAdder module 308 is designed to work in tandem with the DICOMTag2Text module 306. Module 308 receives parameters from fax server 2, including, for example, path, folder, patient name, barcode, IP address of the DICOM Server 2, port number of the DICOM Server 2, local Application Entity name, and remote Application Entity name.

Thus, DICOMfaxadder module 308 preferably reads a TIFF file from the respective folder, and subsequently queries an E-FILM database and creates a DICOM archive that preferably sends a fax to DICOM Server 2. The fax preferably has attached the appropriate patient examination as an additional examination series. The workflow is as follows: the specially barcoded cover page is produced by the DICOMtag2text module 306.

Ancillary software also allows the addition of referring physician information (address, phone, fax) to the DICOM file if examination data are lacking, and are meant to be used by ancillary personnel (e.g., secretaries or assistants to the teleradiologist) to add this information. This feature is significant, particularly, for bi-directional HL-7 feeds. The present invention preferably includes a module that uses an HL-7 feed for speech recognition transcription. For example, if a DICOM patient file contains the referring physician address and telephone/fax information, the proper header is substantially automatically produced by a module included with the speech recognition software, and is preferably entered as part of the actual radiology report and automatically faxed to the referring physician.

Other "ancillary" software modules of the present invention perform such functions as producing the required patient output file (described above). The present invention supports a variety of DICOM servers that receive and digitize medical imaging examinations as DICOM files. For example, the present invention allows the use of EFILM, MEDWEB, and CONQUEST DICOM servers to be used to produce similar databases, such that the present invention can be universally used.

Another feature of the present invention (provided via a hardware/software module) includes a patient information facsimile ("fax") module. Preferably, a dedicated fax server is provided which supports the use of a printed barcode on the cover page of a fax. The barcode is derived from the DICOM tag database of the DICOM image examination. The barcode is preferably read and used to automatically name the fax substantially when received, and automatically formats the fax as a named TIFF file and, thereafter, attaches the TIFF file to an encrypted e-mail letter. In an example embodiment, the fax is processed in a similar way as the scanned paperwork (described above).

In an example embodiment of the fax module of the present invention, the workflow is as follows: a barcode cover page is substantially automatically produced by the present invention when an imaging study is received by, for example, the DICOM server. The cover page is then either 1) automatically uploaded to an FTP site for download by the examination site personnel, 2) automatically printed at the examination site, for example, via an internet printing application, or 3) automatically faxed to the examination site directly. The technologist at the examination site then uses this specially encoded cover sheet to send the corresponding patient paperwork via a typical fax machine to a server operating the present invention. In this way, the present invention enables a remote site to fax paperwork directly into the patient's DICOM examination file. By enabling technologists to fax paperwork, the need for paper scanners and capture programs is obviated, and the process of providing non-digital handwritten patient information to the DICOM examination, and ultimately to the interpreting physician, is greatly simplified.

Figure 8:
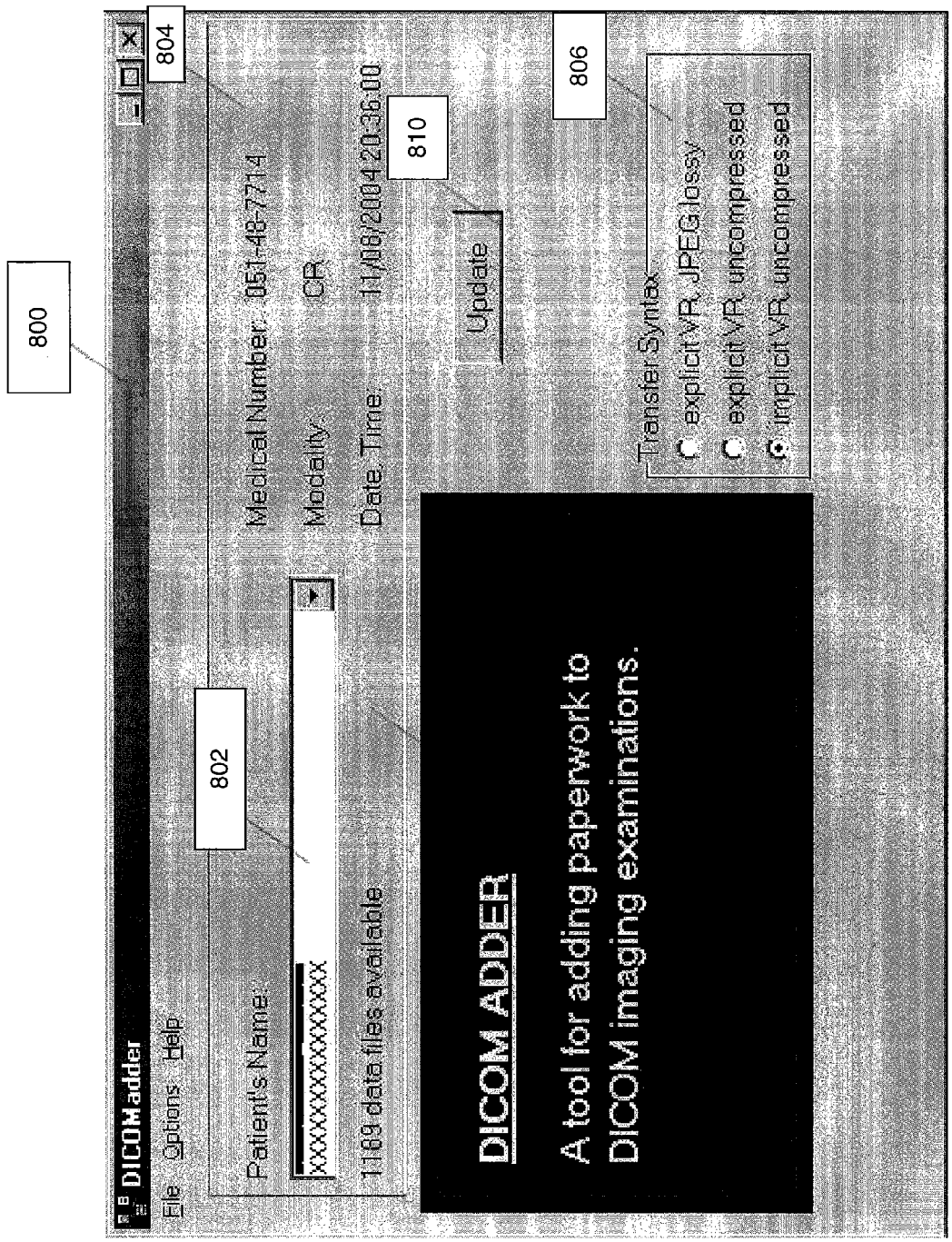
FIG. 8 is an example data entry display screen for selecting a patient and converting image files to files in the DICOM format using the DICOM tags and data of the selected patient in accordance with an embodiment of the present invention.

FIG. 8 is an example data entry display screen 800 provided by the present invention. Display screen 800 is used for enabling a user to select a patient, and to convert one or more image (JPEG) files to files in the DICOM format using the data of the selected patient. As described above, paperwork generated during one or more medical examinations is integrated by the present invention when a user selects a patient and opens image file(s) stored on a remote site (e.g., FTP server 2) or stored locally on the user's computer system. For example, data files are stored on an FTP server or on the local file system containing the values of some DICOM attributes ("TAGS"). These values are applied to the created DICOM files.

Continuing with reference to FIG. 8, display screen 800 includes drop-down list 802 that allows a user to select a specific patient. After a patient is selected, information is preferably displayed in section 804 which represents the patient's medical identification number, the modality of the medical image (e.g., CT, x-ray, or MRI) and the date/time the image was generated. When the user is satisfied that the correct patient is selected, the user selects Transfer Syntax 806 to choose a transfer syntax for the created DICOM file(s). As shown in FIG. 8, the transfer syntaxes provided by the present invention include: explicit VR, JPEG lossy, little endian; explicit VR, uncompressed, little endian; and implicit VR, uncompressed, little endian. All of these represent standard DICOM transfer protocols and syntax. In the example shown in FIG. 8, the default selection is the implicit VR syntax. After the user has selected the patient and the transfer syntax, the user preferably opens one or more JPEG files (via file menu) in order to convert the JPEG file to DICOM format using the data of the selected patient as the DICOM tags.

For example, the menu items "File|Open" displays an open file dialog box. The user selects one or multiple (using the CTRL or SHIFT key) JPEG files. After closing the open dialog by clicking on the OK button, the selected JPEG files are converted to the DICOM standard. The data of the selected patient are included in each DICOM file and the DICOM files are stored on the user's computer system, for example, in a directory location named, "c:\CONVERTOUT." In a preferred embodiment, successfully converted JPEG files are automatically deleted, and the user is notified of the success or failure of the operation.

Also, as displayed in FIG. 8, update button 810 can be selected to reload patient data from the FTP server or user's local computer system, depending upon the location where patient information is stored. This feature is useful for updating patient information (e.g., demographics) over time, and to provide DICOM files that contain current patient information.

In a preferred embodiment of the present invention, the user can configure the present invention to identify the locations of data that are used for generating DICOM files, substantially as described herein. The user can configure the present invention by selecting the menu entry choice "Options|Configure" as shown in FIG. 8. After correctly entering the password, the present invention preferably displays the Configuration Dialog screen 900, as shown in FIG. 9.

Figure 9:
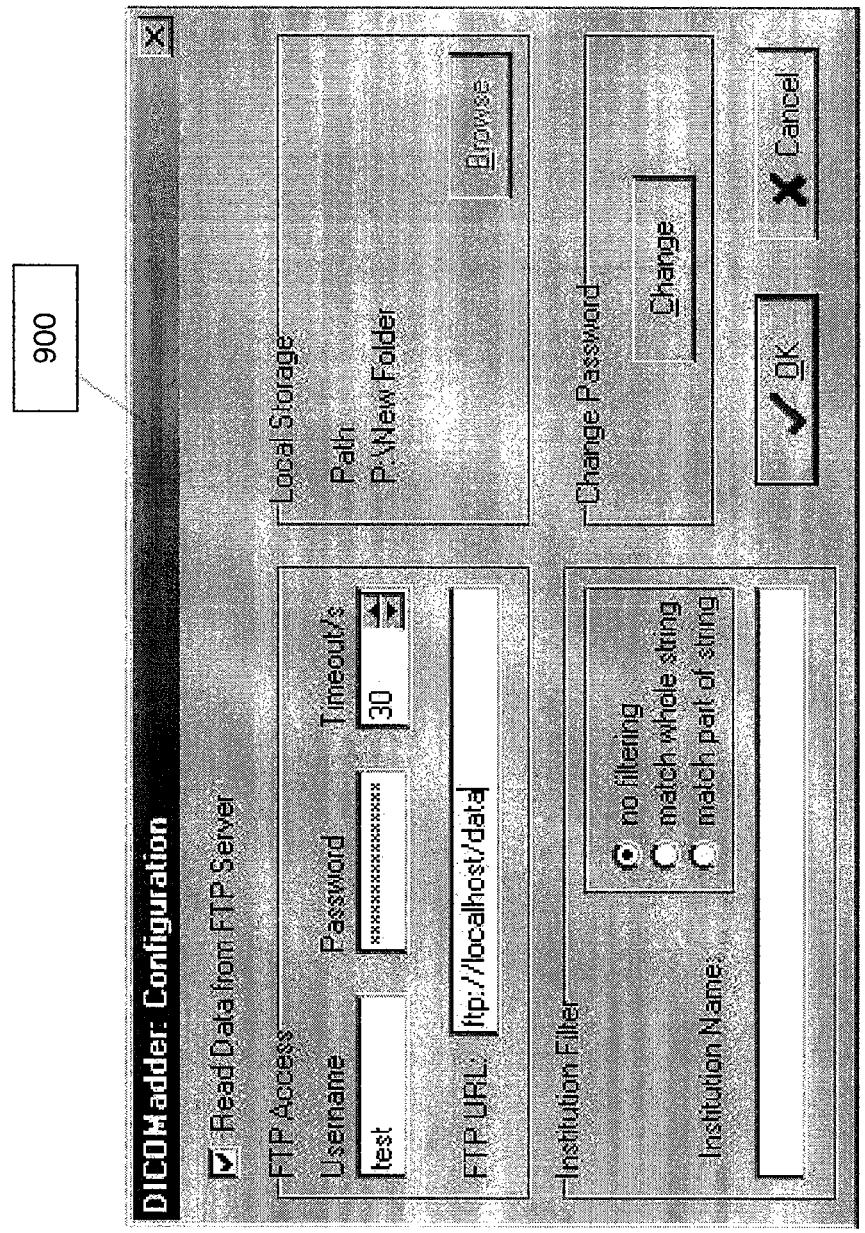
FIG. 9 is an example data entry display screen for configuring features of the present invention in accordance with an example embodiment.

FIG. 9 is an example data entry display screen for, among other things, configuring a location for importing patient-related data into files in the DICOM format in accordance with an embodiment of the present invention. As shown in FIG. 9, "Read data from FTP server" checkbox screen control is provided to define that data are to be imported from an FTP server, and to enable a user to configure FTP access. For example, when the checkbox is selected, the user enters the FTP URL (e.g., complete path, including protocol ftp://), the user name and corresponding password into respective textboxes. Thereafter, the present invention automatically uses the settings to communicate with an FTP server and to initiate a file transfer of patient information. Other options available to the user include changing the timeout for the FTP transfer and configuring an "Institution Filter."

Institution filtering is used to restrict the retrieval of patient data that comply with institutional information defined by the user. In particular, to configure an Institution Filter, the user preferably enters a character string in the "Institution Name" textbox. As shown in FIG. 9, the user selects radio button controls for "no filtering" (any data file is available), "match whole string" (Institution Name in data file must be equal to entered Institution name), or "match part of string" (Institution Name in data file must contain entered value as substring). In an example embodiment, filtering is case-sensitive. This feature is important to preserve patient confidentiality.

As noted above, the present invention supports patient data that are stored locally, in case the user desires not to connect to an FTP server in order to retrieve patient data. As shown in FIG. 9, in case the checkbox "Read data from FTP server" is not checked, the user is able to navigate or "browse" to a local folder that contains the patient data file(s). This folder will be used for storing and retrieving the data files.

Another option provided in display screen 900 is the ability to change a user's password (e.g., by selecting the change password ("Change") button). A dialog box requires the user to enter an old password once and the new password twice. After confirmation, the new password is active.

After the user is satisfied with the configuration settings provided in display screen 900, the user applies the changes. The user preferably selects the button labeled "OK" to apply the changes of the configuration. Alternatively, the "Cancel" button closes the configuration dialog without modifying the configuration.

Thus, the present invention enables users to retrieve patient information and digital forms of paperwork to provide DICOM files that integrate paperwork with medical image records.

Figure 10:
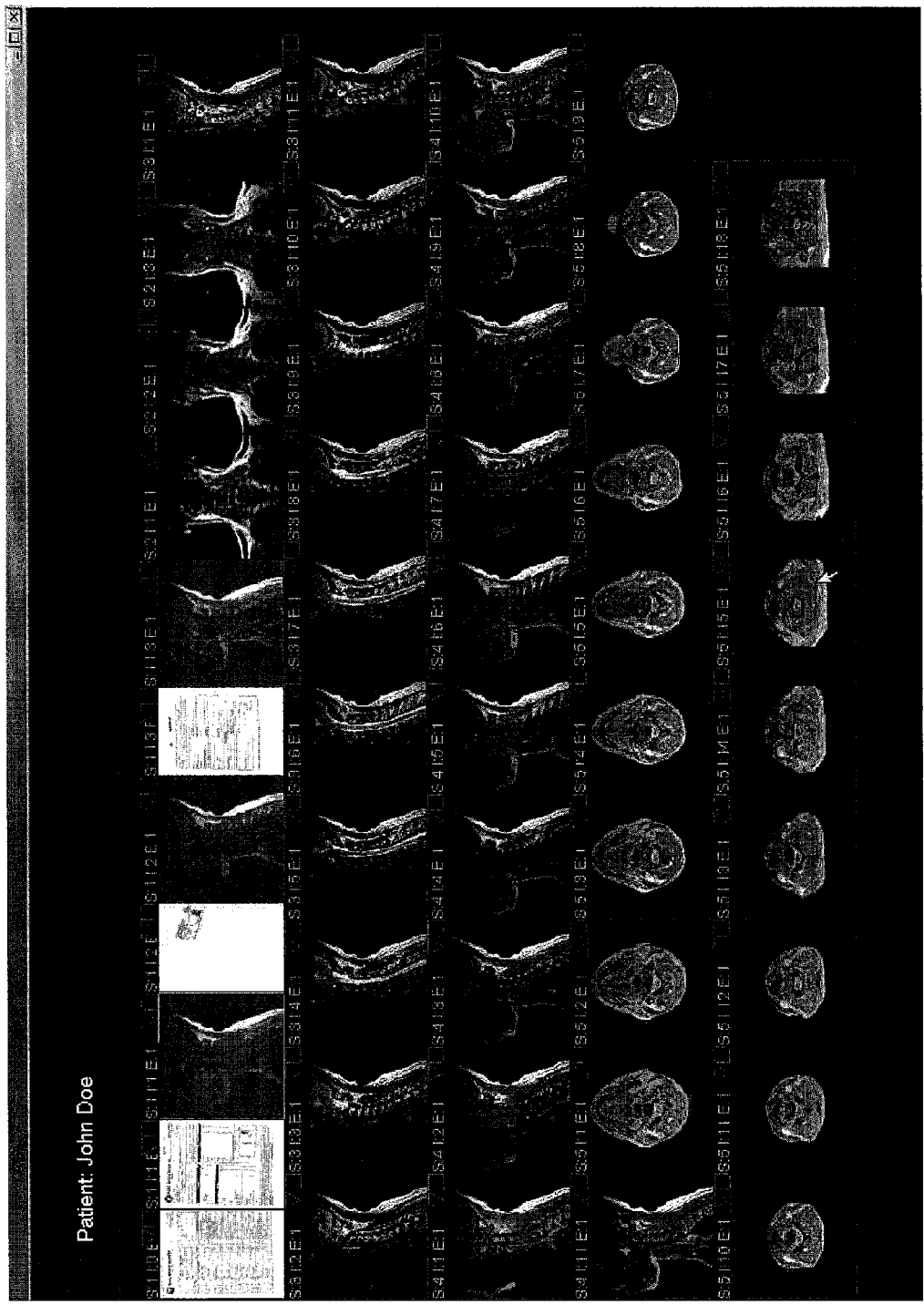
FIG. 10 is an example "thumbnail" view of images comprising patient examination information and medical images displayed simultaneously in the DICOM format, and provides by an example the embodiment of the present invention.

FIG. 10 is an example "thumbnail" view of images comprising patient examination information and medical images in the DICOM format and provided by an example embodiment of the present invention. As shown in FIG. 10, a plurality of neck, spine and brain images are provided along with electronic versions of paperwork. Preferably, a user selects one or more of the images (and/or electronic versions of paperwork) and enlarged versions are provided for improved viewing. In this way, the viewing of hand-written paper data are provided simultaneously when medical images are viewed.

In an effort to improve the flexibility and availability of the present invention, an internet-based embodiment is preferably provided on information processor 2 and available for users establishing a communication session with information processor 2 using standard web browsing software. FIGS. 11A-11F illustrate example display screens and reports that are provided in accordance with an internet, web-based embodiment of the present invention.

Figure 11A:
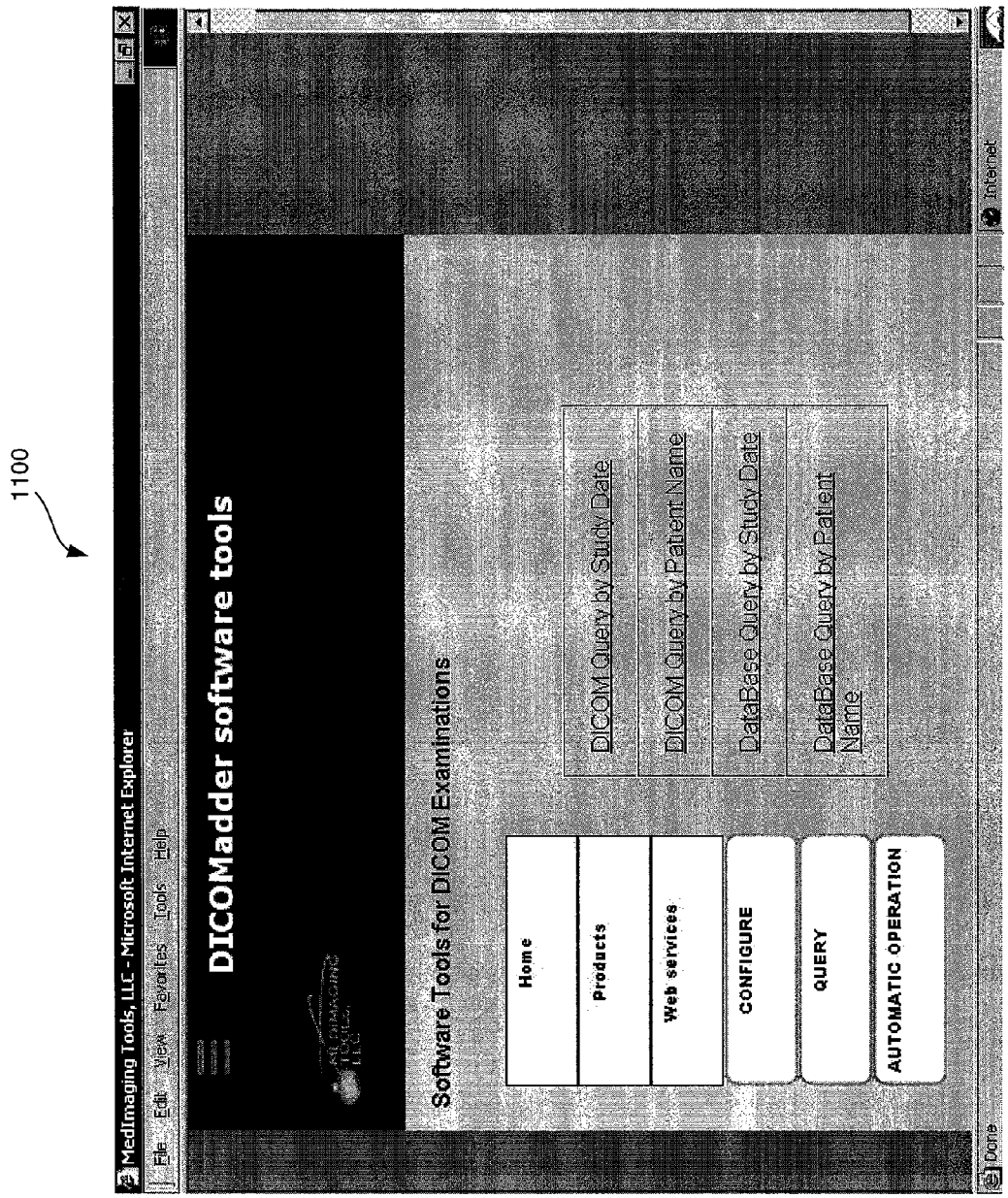

FIG. 11A illustrates an internet web-based display screen 1100 of the present invention that enables a user to perform queries for DICOM records (i.e., integrated image files and ancillary information) and records stored on database 8 which may or may not have corresponding integrated DICOM records. Preferably, display screen 1100 is provided to a user who has selected a graphic screen control (i.e., a button) for performing a query. The choices illustrated in screen 1100 include DICOM Query by Study Date, DICOM Query by Patient Name, DataBase Query by Study Date and DataBase Query by Patient Name.

Figure 11B:
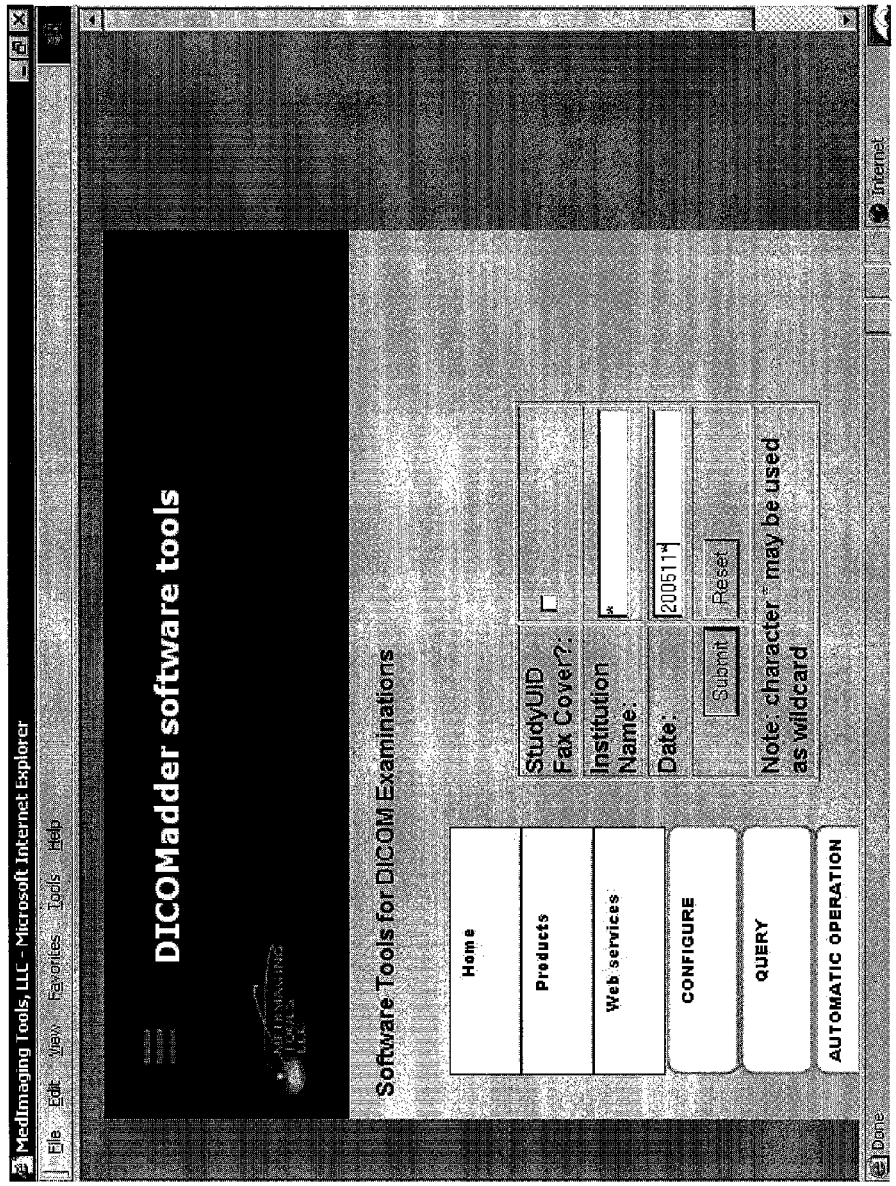

FIG. 11B illustrates an example display screen 1102 that is provided to a user who has selected DICOM Query by Study Date from display screen 1100. The user has the option in display screen 1102 to select a control to generate a fax cover page (formatted with corresponding bar code), and specifies information for the query. For example, and as shown in FIG. 11B, the user identifies in textbox control an institution name 438 and/or the Study Date 432 of interest. In the example web-based embodiment shown FIG. 11B, a so-called "wildcard" character (e.g., "*") can be submitted in the textbox controls to represent any character in the query. In the example shown in FIG. 11B, any institution name ("*") is identified by the user, and the date is any day within the month of November, 2005 ("2000511*"). After the user presses the submit button control, the query is executed on server 2, and the results are displayed (substantially as displayed in FIG. 11C). Alternatively, the user can select the reset button to clear the entries and begin again.

FIG. 11C illustrates an example query result display screen 1104 provided in accordance with the web-based embodiment of the present invention. As shown in FIG. 11C, a series of columns are provided that include the UID 426, institution 438, modality 428, patient name 418 and study date 432. Display screen 1104 further includes a column for enabling a user to create a fax cover sheet, preferably formatted as a hyperlink. This feature enables a user to search for a particular study, and, thereafter, generate a fax cover sheet formatted with a respective bar code for future use.

Figure 11D:
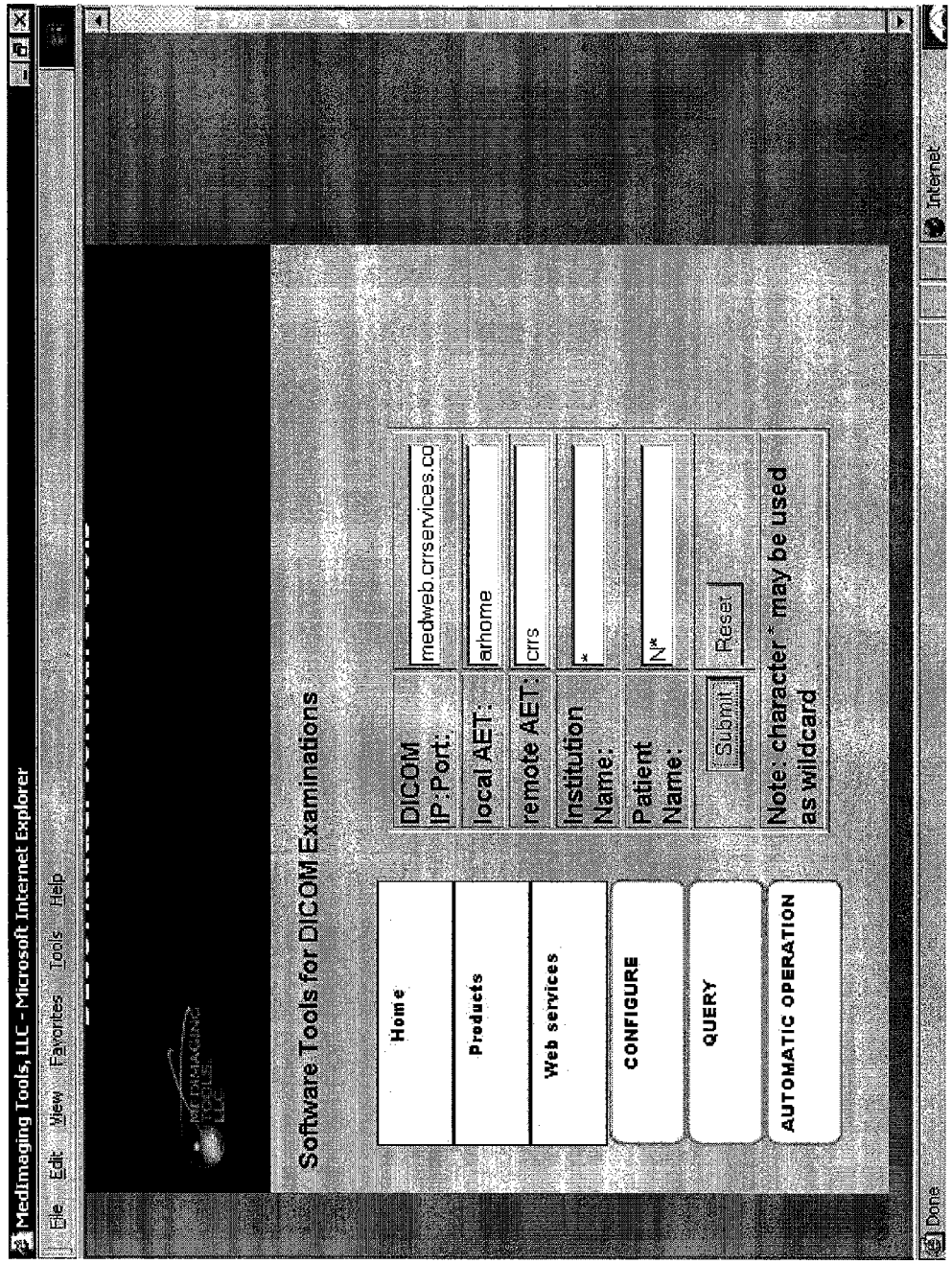

FIG. 11D illustrates an example display screen 1106 that is provided to a user who has selected DICOM Query by Patient Name from display screen 1100. The user has the option in display screen 1106 query for IP 408, Local Entity Title 414, DICOM server Entity Title 416, Institution Name 438 and Patient Name 418. Upon selecting the submit button, a report, substantially as displayed in FIG. 11C (with data corresponding to the query submitted in FIG. 11D) is provided.

Figure 11E:
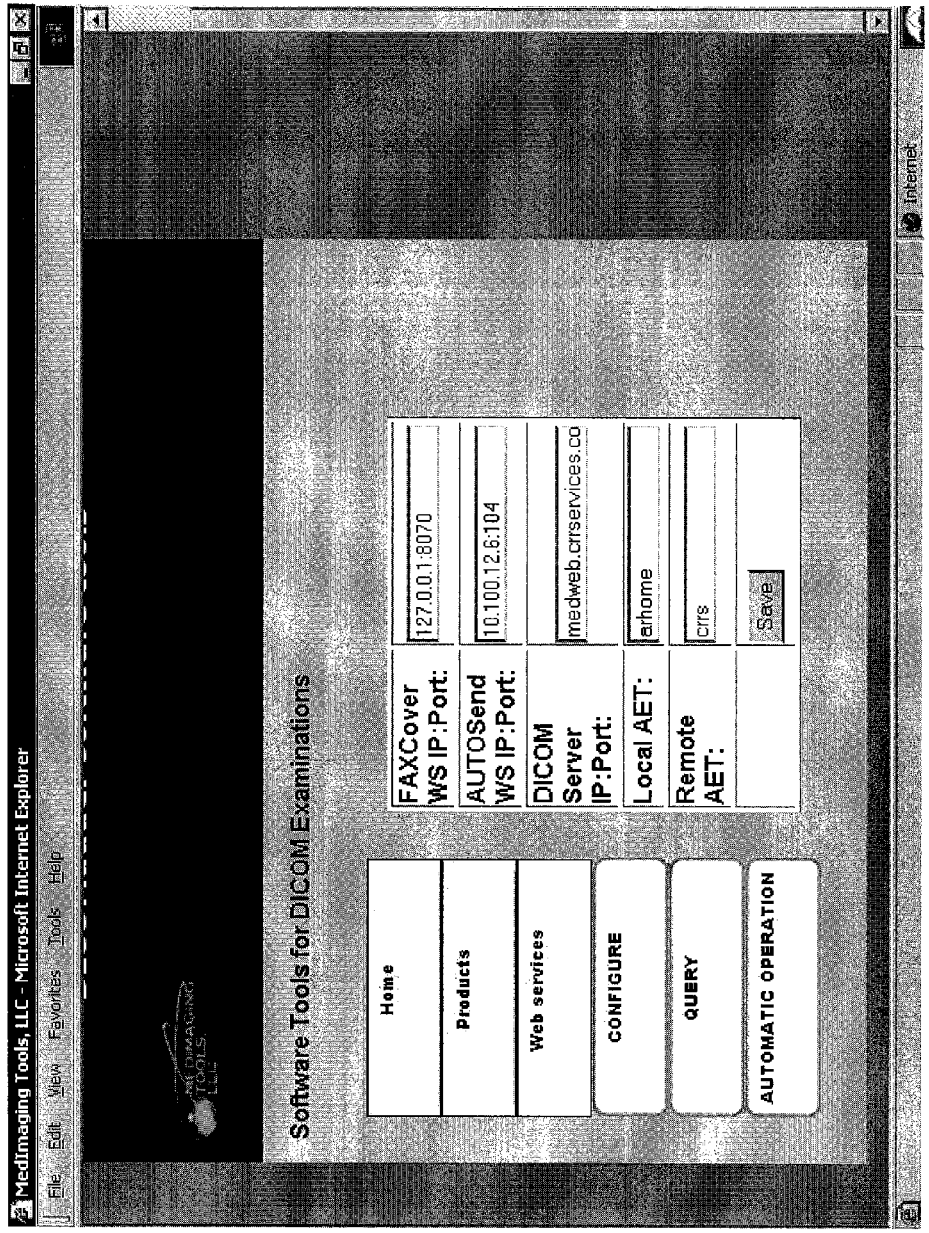

FIG. 11E shows an example display screen 1108 that is provided to a user who has selected a graphical screen control for configuring ("CONFIGURE") the web based application, such as in display screen 1100. In the example display screen 1108 shown in FIG. 11E, a textbox control is provided for an IP address and port number for the fax server 2 for generating fax cover pages. Further a textbox control is provided for an IP address and port number for information processor 2 for automatically transmitting DICOM integrated files. Moreover, a textbox control is provided for the DICOM server 2 IP and port 410/412, and Local Entity Title 414 and DICOM server Entity Title 416. The user preferably selects the save button to ensure the settings are provided in the future.

Figure 11F:
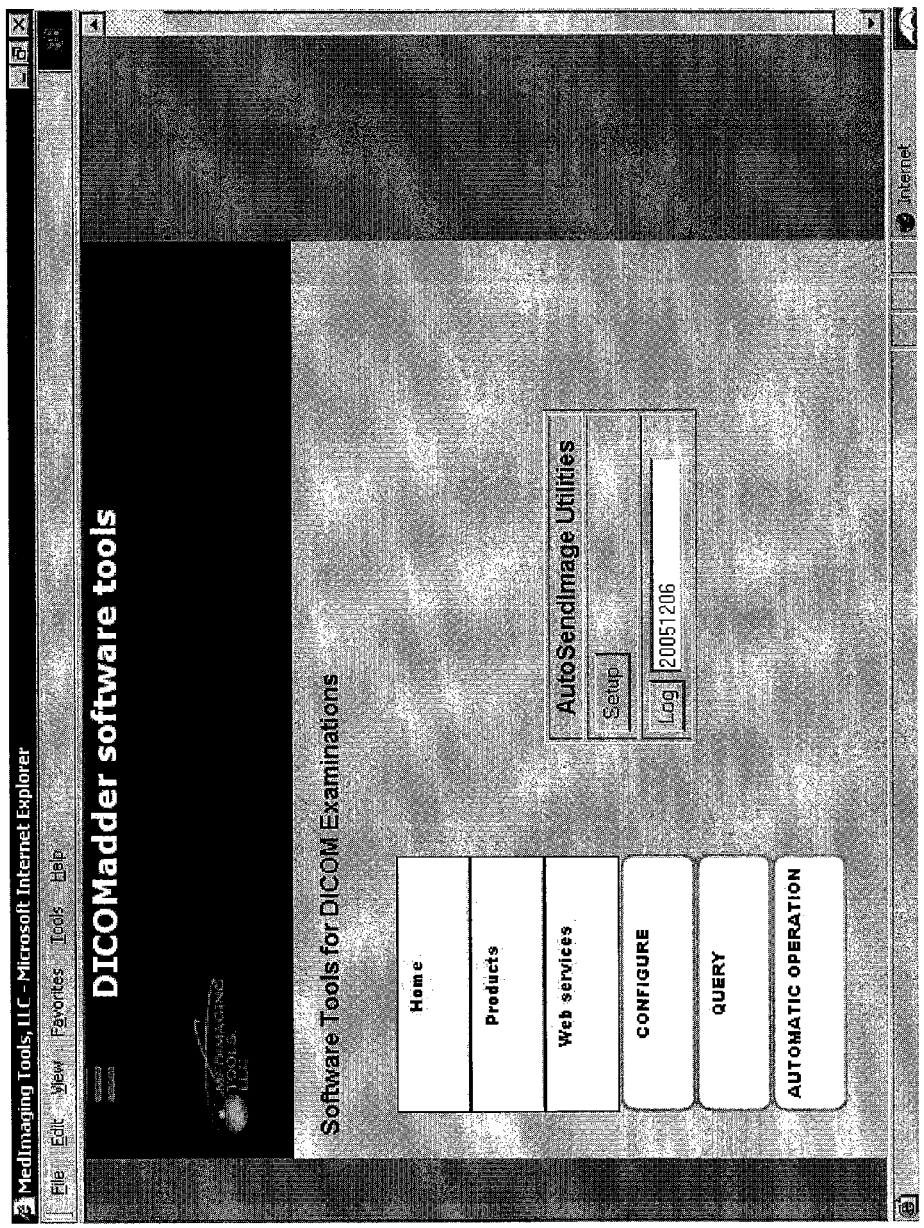

FIG. 11F shows an example a web-based display screen 1110 that is preferably used for automatically uploading images to DICOM server 2 in accordance with the present invention. Using the setup button, the user can identify a folder to identify a location where image files, such as TIFF files or JPEG files, will be stored. As described above, when an image file is recognized, module 302 preferably converts it to DICOM format and transmits the formatted file to DICOM Server 2. In a preferred embodiment, module 302 recognizes when the name of the image file employs a particular format, such as PatientName-PatientID-StudyUID (e.g., names of data fields that represent a patient and study), and module 302 preferably uses these data when converting an image file to the DICOM format. In accordance with the embodiment shown in FIG. 11F, the user can specify this information using a web-based display screen. Further, the user can identify a specific date (including by using a wildcard character, as described above), and, thereafter, select the log button to review a history of file activity.

Thus, as shown in the example display screens 11A-11F, the present invention provides a convenient and secure internet-based embodiment that is operable using standard web browser software.

A discussion regarding technical details regarding an embodiment of the present invention is now provided to further describe the invention.

The present invention contains an interface as a COM- and Automation-Server (COM refers herein to the known Component Object Model). The interface enables a technical user to remotely control the present invention without the need for an interactive session, substantially as described. For example, one or more computer software programs or scripts can be developed to automate the functions and configuration of the present invention.

More particularly, a user can employ one or more automation functions to define various features of the present invention that are to be performed automatically. The following example lists functions that are provided in an example embodiment of the present invention: SetInputFolder; SetOutputFolder; SetLookupTable; SetErrorFolder; SetTransferSyntax; and ProcessFolder. Other functions not listed herein are envisioned which support other functionality of the present invention, and is or will become apparent to one skilled in the art. A brief description of the above-listed functions is provided below.

The SetInputFolder function enables a user to define an "input" folder or location on a computer system where JPEG files are to be expected and, once retrieved, to be converted to DICOM. In an example embodiment, the following syntax is used: int SetInputFolder(BSTR DirName). As used in an example embodiment, "DirName" indicates the path or the directory where the JPEG files are stored. Preferably, DirName is formatted as an absolute path name. If SetInputFolder succeeds, the computer system preferably returns a value of 0, otherwise an Errorcode is returned (−1), in case the specified folder does not exist.

The SetOutputFolder function enables a user to define an "output" folder or location on a computer system where the converted DICOM files are to be stored. In an example embodiment, the following syntax is used: int SetOutputFolder(BSTR DirName). As used in an example embodiment, DirName indicates the path of the target directory for the DICOM files. Preferably, DirName is formatted as an absolute path name. If SetOutputFolder succeeds, the computer system preferably returns a value of 0, otherwise an Errorcode is returned (−1), in case the folder does not exist.

The SetLookupTable function enables a user to define the path of a lookup table that maps the variable, "siteIDs" to Institution Names. In an example embodiment, the following syntax is used: int SetLookupTable(BSTR FileName). As used in an example embodiment, "FileName" indicates the path where a filename of a lookup table file is stored. If SetLookupTable succeeds, the computer system returns a value of 0, otherwise an Errorcode is returned (−2), in case the file does not exist, or (−3) in case the file could not be parsed.

The SetErrorFolder function enables a user to define an error folder where JPEG files are to be copied, in case no matching data file can be found on an FTP server. In an example embodiment, the following syntax is used: int SetErrorFolder(BSTR DirName). As used in an example embodiment, "DirName" indicates the path of the directory where JPEG files without a match are located. If SetErrorFolder succeeds, the computer system returns a value of 0, otherwise an Errorcode is returned (−1) in case the folder does not exist.

The SetTransferSyntax function enables a user to define which transfer syntax shall be used with the present invention. In an example embodiment, the following syntax is used: int SetTransferSyntax(int Value). As used in an example embodiment, "Value" represents a number that specifies the transfer syntax according the following: Value VR Compression Byte Order—0 explicit JPEG lossy little endian, 1 explicit none little endian, 2 implicit none little endian. On success, the SetTransferSyntax functions causes the computer system to return the value for the TransferSyntax, otherwise an error code is returned (−6), in case the value for the TransferSyntax is out of range.

The ProcessFolder function enables a user to convert JPEG files in the inputfolder to DICOM and to apply the information of the matching data files on the FTP server. In an example embodiment, the following syntax is used: int ProcessFolder( ). If ProcessFolder succeeds, the computer system returns the number of successfully converted files, otherwise an Errorcode is returned (−3) in case no lookup file is available, (−4) in case any of the required folders wasn't defined or doesn't exist, (−5) in case no access to the data files was possible (FTP connection or access failed or no access to file system folder), (−6) in case if no supported TransferSyntax is specified.

Of course, one skilled in the art will recognize that the functions described above illustrate ways to automate tasks and configuration of the present invention. Other functions and techniques will become apparent to one skilled in the art for providing features, such as described herein.

Although the present invention has been described in relation to particular embodiments thereof, many other variations and modifications and other uses will become apparent to those skilled in the art. It is preferred, therefore, that the present invention be limited not by the specific disclosure herein.

What is claimed is:

1. A method for receiving a DICOM image file from a first DICOM storage service class user, employing rules on the DICOM image file and forwarding the DICOM image file to a second DICOM storage service class user in accordance with the rules, the method comprising:

providing at least one automated processor operatively coupled to non-transitory processor readable media;

receiving, by the at least one automated processor from a user via an electronic user interface:

router configuration information, the router configuration information representing at least a DICOM storage service class provider for receiving the DICOM image file from the first DICOM storage service class user;

remote server configuration information, the remote server configuration information representing a plurality of computing devices operable to send or receive DICOM image files over a communication network;

routing rules information, the routing rules information representing first data conditions for transmitting to at least one of the plurality of computing devices the DICOM image file; and replacement rules information, the replacement rules information representing second data conditions for modifying at least one DICOM tag data value in the DICOM image file;

receiving, by the at least one automated processor over the communication network the DICOM image file from the first DICOM storage service class user in accordance with the router configuration information, wherein the DICOM image file represents at least part of a medical study for a patient, and, further wherein the DICOM image file is in conformance with DICOM as existing on Feb. 22, 2005;

examining, by the at least one automated processor, the at least one DICOM tag data value in the DICOM image file and modifying, by the at least one automated processor, the at least one DICOM tag data value in the DICOM image file in accordance with the replacement rules information; and examining, by the at least one automated processor, the routing rules information; and routing, by the at least one automated processor, the modified DICOM image file to the one of the plurality of computing devices in accordance with the at least one modified DICOM tag data value in the DICOM image file and the routing rules information.

2. The method of claim 1, wherein the router configuration information includes at least one of a port number, a local application entity title, and a default server name.

3. The method of claim 2, wherein the DICOM image filed is received by a computing device represented by the default server name in the event no matching routing rules are met.

4. The method of claim 1, further comprising:
storing the user replacement rules information in at least one database;
storing the routing rules information in the at least one database;
storing the remote server configuration information in the at least one database; and
storing the router configuration information in the at least one database.

5. The method of claim 1, wherein the communication network is the internet.

6. The method of claim 1, wherein the electronic user interface includes graphical screen controls enabling the user to add, edit or delete the remote server configuration information, the routing rules information and the replacement rules information.

7. The method of claim 1, wherein the first and second data conditions are based upon values or formatting of data in DICOM data fields.

8. The method of claim 1, wherein the router configuration information includes an internet protocol address, an application entity title, and a port number.

9. The method of claim 1, wherein the DICOM image file is received in one DICOM format and routed in the one DICOM format.

10. The method of claim 9, wherein the DICOM format is JPEG lossless, Explicit VR Little Endian, Implicit VR Little Endian or JPEG Lossy.

11. The method of claim 1, further comprising:
examining a histogram of the DICOM image;
calculating an average pixel value and standard deviation; and
deriving an optimum window size and position based on the average pixel value and the standard deviation.

12. A system for receiving a DICOM image file from a first DICOM storage service class user, employing rules on the DICOM image file and forwarding the DICOM image file to a second DICOM storage service class user in accordance with the rules, the system comprising:

a computing device including an electronic user interface operable on the computing device to receive from a user:
router configuration information that represents at least a DICOM storage service class provider for receiving the DICOM image file from the first DICOM storage service class user;
remote server configuration information that represents a plurality of computing devices operable to send or receive DICOM image files over a communication network;
routing rules information that represents first data conditions for transmitting to at least one of the plurality computing devices the DICOM image file; and
replacement rules information that represents second data conditions for modifying at least one DICOM tag data value in the DICOM image file;

wherein the computing device is programmed and configured to:

receive over the communication network the DICOM image file from the first DICOM storage service class user in accordance with the router configuration information, wherein the DICOM image file represents at least part of a medical study for a patient, and, further wherein the DICOM image file is in conformance with DICOM as existing on Feb. 22, 2005;

examine the at least one DICOM tag data value in the DICOM image file and modify the at least one DICOM tag data value in the DICOM image file in accordance with the replacement rules information; and examine the routing rules information and route the modified DICOM image file to the one of the plurality of computing devices in accordance with the at least one modified DICOM tag data value in the DICOM image file and the routing rules information.

13. The system of claim 12, wherein the router configuration information further includes at least one of a port number, a local application entity title, and a default server name.

14. The method of claim 13, wherein the DICOM image filed is received by a computing device represented by the default server name in the event no matching routing rules are met.

15. The system of claim 12, further comprising a database that stores the user replacement rules information, the routing rules information, the remote server configuration information and the router configuration information.

16. The system of claim 12, wherein the communication network is the internet.

17. The system of claim 12, wherein the electronic user interface includes graphical screen controls enabling the user to add, edit or delete the remote server configuration information, the routing rules information and the replacement rules information.

18. The system of claim 12, wherein the first and second data conditions are based upon values or formatting of data in DICOM data fields.

19. The system of claim 12, wherein the router configuration information further includes an internet protocol address, an application entity title, and a port number.

20. The system of claim 12, wherein the DICOM image file is received in one DICOM format and routed in the one DICOM format.

21. The system of claim 20, wherein the DICOM format is JPEG lossless, Explicit VR Little Endian, Implicit VR Little Endian or JPEG Lossy.

22. The system of claim 12, further comprising an automatic window size and position module operable to examine a histogram of the DICOM image, to calculate an average pixel value and standard deviation and to derive an optimum window size and position based on the average pixel value and the standard deviation.

* * * * *